(12) United States Patent
Yamaguchi et al.

(10) Patent No.: US 7,405,835 B2
(45) Date of Patent: Jul. 29, 2008

(54) HIGH-ACCURACY PATTERN SHAPE EVALUATING METHOD AND APPARATUS

(75) Inventors: Atsuko Yamaguchi, Kodaira (JP); Hiroshi Fukuda, Tokyo (JP); Osamu Komuro, Hitachinaka (JP); Hiroki Kawada, Tsuchiura (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 11/808,627

(22) Filed: Jun. 12, 2007

(65) Prior Publication Data

US 2007/0242885 A1 Oct. 18, 2007

Related U.S. Application Data

(63) Continuation of application No. 11/322,559, filed on Jan. 3, 2006, now Pat. No. 7,230,723.

(30) Foreign Application Priority Data

| Jan. 4, 2005 | (JP) | ............................. 2005-000029 |
| Nov. 29, 2005 | (JP) | ............................. 2005-343047 |

(51) Int. Cl.
*G01B 11/24* (2006.01)
*G01N 23/00* (2006.01)
*G06K 9/46* (2006.01)

(52) U.S. Cl. ...................... 356/605; 356/600; 356/601; 250/492.3; 250/300; 382/199

(58) Field of Classification Search ......... 356/600–625, 356/237.2, 237.4, 237.5; 250/307, 310–311, 250/492.1, 492.2, 492.3
See application file for complete search history.

(56) References Cited

U.S. PATENT DOCUMENTS

| 5,585,211 | A | * | 12/1996 | Firstein et al. ................ 430/30 |
| 5,805,728 | A | * | 9/1998 | Munesada et al. ........... 382/199 |
| 5,896,188 | A | | 4/1999 | McCullough |
| 5,969,357 | A | | 10/1999 | Todokoro et al. |
| 6,411,377 | B1 | | 6/2002 | Noguchi et al. |
| 6,473,162 | B1 | | 10/2002 | Masaki et al. |
| 6,516,528 | B1 | | 2/2003 | Choo et al. |
| 6,781,688 | B2 | * | 8/2004 | Kren et al. ................ 356/237.4 |
| 6,839,470 | B2 | * | 1/2005 | Ikeda ......................... 382/266 |

(Continued)

OTHER PUBLICATIONS

Yamaguchi, A. et al., Metrology of LER: Influence of Line-Edge Roughness (LER) on Transistor Performance, Proceedings of SPIE Reprint, 2004, pp. 468-476, vol. 5375, (SPIE, Bellingham, WA).

(Continued)

*Primary Examiner*—Sang H. Nguyen
(74) *Attorney, Agent, or Firm*—Antonelli, Terry, Stout & Kraus, LLP.

(57) ABSTRACT

A quantity (or dispersion value) of a distribution of edge position due to random noise is expected to be reduced statistically to 1/N when N edge position data items are averaged. Using this property, the single page image is averaged in a vertical direction with various values of parameter S, and then the edge roughness index is calculated. The S-dependence of the edge roughness index is analyzed and a term of a dispersion value directly proportional to 1/S is determined as being due to noise.

18 Claims, 12 Drawing Sheets

U.S. PATENT DOCUMENTS

| | | |
|---|---|---|
| 6,909,791 B2 | 6/2005 | Nikitin et al. |
| 6,929,892 B2 | 8/2005 | Shishido et al. |
| 7,049,589 B2 | 5/2006 | Yamaguchi et al. |
| 7,269,287 B2 * | 9/2007 | Shishido et al. ............ 382/207 |
| 2002/0097913 A1 * | 7/2002 | Ikeda ........................ 382/199 |
| 2003/0021483 A1 | 1/2003 | Yamaguchi et al. |
| 2005/0275850 A1 | 12/2005 | Bischoff et al. |

OTHER PUBLICATIONS

Bunday, Benjamin D., Determination of Optimal Parameters for CD-SEM Measurement of Line Edge Roughness, Proceedings of SPIE Reprint, 2004, vol. 5375 (SPIE, Bellingham, WA).

* cited by examiner

PRIOR ART

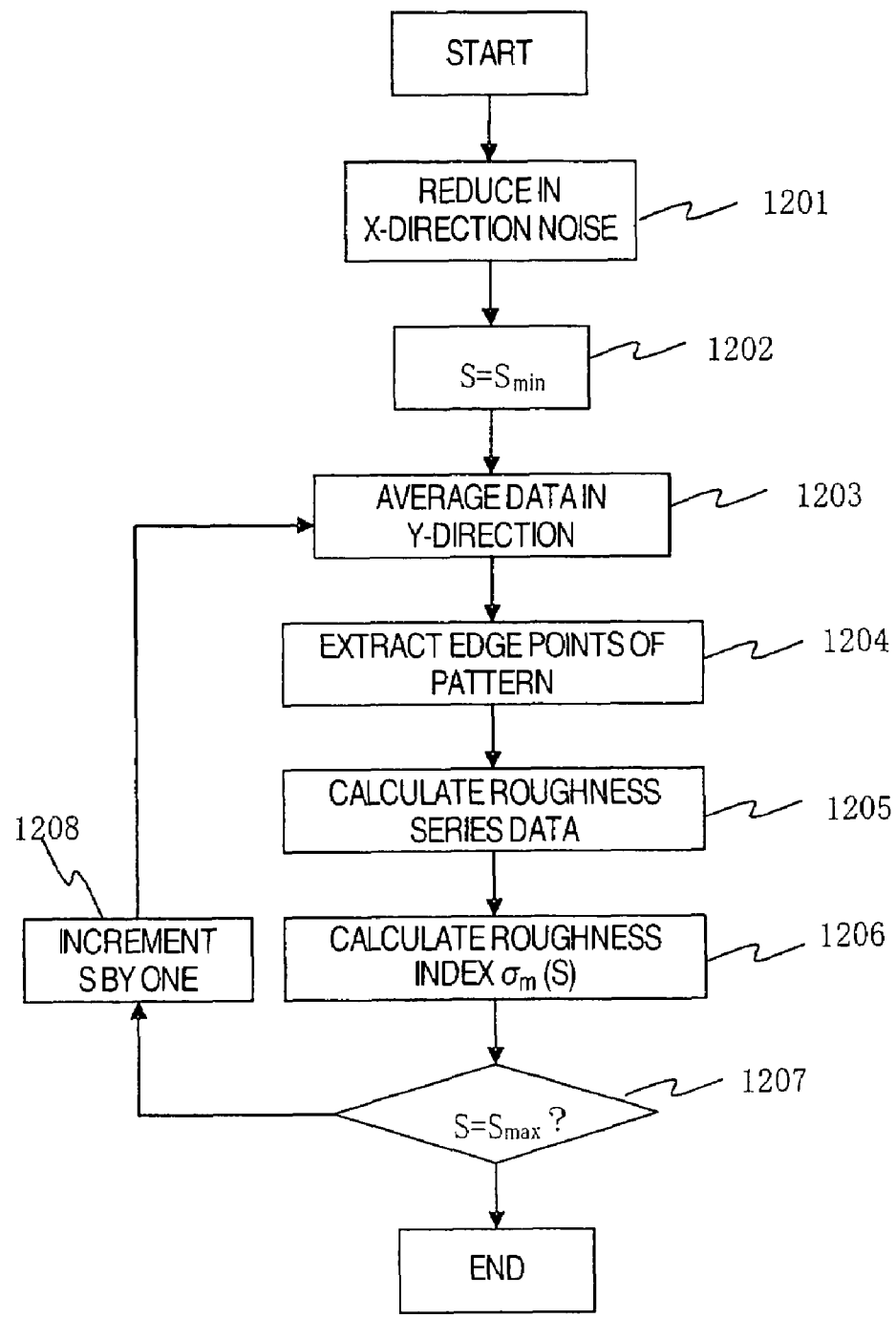

HIGH-ACCURACY PATTERN SHAPE EVALUATING METHOD AND APPARATUS

CROSS-REFERENCE TO RELATED APPLICATION

This application is a Continuation application of application Ser. No. 11/322,559, filed Jan. 3, 2006, now U.S Pat. No. 7,230,723 which claims priority from Japanese patent applications JP 2005-000029, filed on Jan. 4, 2005, and JP2005-343047, filed on Nov. 29, 2005, the contents of which are incorporated herein by reference in their entirety.

BACKGROUND OF THE INVENTION

The present invention relates to fine pattern examining methods and apparatus using detailed shape or size measurement based on non-destructive observation and image processing, with a scanning microscope and methods of evaluating the examining apparatus.

In semiconductor and other industries, evaluation of fine roughness of randomly occurring pattern edges called edge roughness has been required as the pattern processing sizes become finer. Especially, in semiconductor process it has been known that a local fluctuation of a line width or line width roughness occurring from a (line) edge roughness or a line's right and left edge roughness of a gate or interconnect pattern will greatly influence the device performance. Thus, even in the pattern shape evaluation of the semiconductor process, the line-edge or line width roughness need be measured with high accuracy.

In order to measure the line-edge or line width roughness, however, a set of points representing a pattern edge need be obtained from an observation image displayed on a scanning electron microscope. Random noise occurring in the image acquisition will greatly influence this work. As will be described later in more detail, the influence of the random noise will appear as a bias quantity of the roughness index. A measured value of the roughness will be greater than that obtained from the shape of a real observation pattern.

The bias quantity has been a question in recent years under the following circumstances although it does not come into question when the real roughness value is much greater than the bias quantity. First, damage to a specimen or changes in the dimensions of the specimen (due to pattern shrinkage, charging, adhesion of organic molecules, etc.) due to irradiation of the specimen with an electron beam can be a problem. In order to prevent this damage or size changes, the observation should be made with as small a dose of electron beam irradiation as possible. If the dose of electron beam irradiation is less, however, the ratio in strength of signal to noise (S/N ratio) becomes smaller. Second, there are demands for observation of only higher frequency components of the roughness. When the higher frequency components of the roughness are observed, or a high frequency roughness or short-period roughness is observed, the roughness will be measured on a short line. Then, since no longer-period components are measured, the roughness will be measured on a short line. As a result, the roughness value itself will be smaller. In contrast, since the roughness bias quantity due to noise is a fluctuation quantity per edge point, the bias quantity will not become smaller even when the measured line length is reduced. In other words, if the roughness in the high frequency area is intended to be measured, the bias due to noise will increase relatively. Under these circumstances, it is necessary to eliminate the influence of random noise from the obtained measured value, and calculate a value of the real roughness of the observation pattern.

Simultaneously, there are demands for quantifying noise itself for the purpose of evaluating the performance of the measuring instrument.

In summary, it is necessary to separately take a quantity of roughness and the influence of noise actually present in the observation pattern present in the observation pattern from the index of the edge roughness observed usually.

In the following, a method of generally calculating the index of line-edge or line width roughness, the influence of random noise on the value of the calculated index value, and a conventional method of separating the index value and the random noise will be described.

The edge of a line pattern is calculated as follows. First, the pattern is observed from above with the scanning electron microscope. Let y direction be the direction of a line in a two-dimensional signal intensity distribution obtained and let x direction be the direction perpendicular to the direction of the line. An x-direction distribution of the signal intensity with y as a constant is referred to as a profile of the signal intensity. Such profiles are arranged at constant intervals in the y-direction. When a y-coordinate is specified, a corresponding profile is determined uniquely. FIG. 1 shows a relationship in correspondence between profile and actual pattern cross-sectional view. An upper sub-view of FIG. 1 illustrates a profile actually obtained and a lower part of FIG. 1 shows a cross-sectional view of a line pattern corresponding to the profile. The edge of a line pattern corresponds to a peak of the profile. When an edge roughness is analyzed, edge points are defined according to a given algorism on the profile obtained by actual measurement. Thus, the edge point defined according to the algorism can not necessarily coincide with a peak appearing on the profile. When a value is specified (and referred to as i) on the y-coordinate is specified, an x-coordinate of a point corresponding to the edge can be calculated for the corresponding profile. Then, y-coordinates can be specified at constant intervals and then pattern edges can be extracted one after another from the corresponding profiles, thereby obtaining series data of the pattern edge. FIG. 2 schematically illustrates an enlarged view of a part of a line pattern observed on a SEM image. FIG. 2 illustrates obtaining series data $\Delta x_i$; $\Delta x_1$, $\Delta x_2$, . . . each indicative of a difference between a straight line approximating series data of an edge and a respective one of actual pattern edge positions. The approximate straight-line comprises a set of averaged values of the edge points, and $\Delta x_i$ corresponds to a deviation of an edge point in a specified profile from the averaged value. FIG. 3 comprises a FIG. 2 viewed in perspective. The width of the line pattern is represented by an interval between right and left approximate straight-lines. A (local) line width on a specified profile is represented by a series difference $w_i$ ($=w_1$, $w_2$, . . . ) between the right and left edge series.

Indexes representing degrees of line-edge roughness and line width roughness will be described together as a roughness index in the following. As roughness indexes, ($\Delta x_1$, $\Delta x_2$, . . . ) or ($w_1$, $w_2$, . . . ) is regarded as a set of data and a standard deviation obtained from these data values or three times the standard deviation is generally used. Even at present, these indexes are used in the resist materials and in the screening of a process. In addition, in the future, it is considered that even in the dimension check of the mass production process not only the conventional simple averaged line width or the line's CD (Critical Dimension) but also the roughness indexes need be checked. At this time, an index of the line-edge or line width roughness need be calculated with high accuracy. As shown by non-patent literature 1 shown later, the performance of a transistor is predictable from the values of the indexes of the line width roughness, but also in this case, a high-accuracy width roughness need be obtained.

Proc. SPIE 5375 (2000), pp468-476 discloses a technique for setting measurement parameters comprising an extent of a measurement area in the roughness measurement and that of an interval at which the edge point is sampled, based on a spatial frequency distribution of roughness. In addition to these measurement parameters, the device performance and more particularly an extent of noise influence the measured values of the actual roughness indexes. Proc. SPIE 5375 (2004), pp515-533 shown later discloses a view that the positions of the edge points which will be observed on each profile have a distribution round a real edge point. Such distribution is considered as arising from noise. Let $\sigma_e$ be a distribution (or standard deviation) of the observed edge point positions around the actual position. Then, an edge roughness index $\sigma_m$ observed is given by $$\sigma_m = \sqrt{\sigma_0^2 + \sigma_e^2} \qquad \text{Ex. 1}$$

where $\sigma_0$ is the actual edge roughness index (represented by a standard deviation).

That is, the observed value of the edge roughness index is larger than the real value. In the present description text, a change of the edge roughness index from its real value is referred to as a bias of the edge roughness. Occurrence of the bias is mainly due to noise.

Similarly, this applies when an object is not edge roughness, but line width roughness. In the case of the line width roughness, observed variation in the positions of the right and left edge points adds to that of the local line widths and the observed value of the line width roughness index is larger than the real value. In the following, the edge roughness will be mainly discussed.

Even when a bias is present in the observed value of the edge roughness, the edge roughness index still represents the feature of the pattern shape. When $\sigma_0$ becomes smaller, $\sigma_m$ becomes rather closer to $\sigma_e$, and does not represent an extent of the edge roughness correctly. When a pattern of small line-edge roughness is measured, it is necessary to eliminate the influence of the edge roughness bias and obtain as close a value to the real index value $\sigma_0$ as possible. Even when an index (such as, for example, a deviation average) other than the above example (or standard deviation) is used as that of the line-edge or line width roughness, the observed value will likewise have a bias that reflects, noise. In the present invention, standard deviation will be used as an index of roughness in every case for purposes of easy understanding.

Proc. SPIE 5375 (2004), pp515-533 discloses a method of separating a real value $\sigma_0$ and a term $\sigma_e$ due to noise from a measured value $\sigma_m$ of expression 1. In this method, an object pattern is observed a plurality of times, thereby obtaining a plurality of images corresponding to two-dimensional signal intensity distributions. Then, all these data are added up (more particularly, the two-dimensional intensity distributions are either added or averaged) and edge point positions are obtained which considered to be close to the real edge point positions (referred to as averaged edge points temporarily) from the obtained added-up data. The edge point positions obtained by observation from data for a plurality of pages of data are distributed around the averaged edge point. A standard deviation of this distribution is then calculated and represented by $\sigma_e$.

As described above, since the line-edge or line width roughness influences the characteristics of a semiconductor device, the value of the line-edge or line width roughness can be used as a criterion for determining whether the semiconductor manufacturing process is good or not. Thus, in order to evaluate the process, it is necessary to calculate a real roughness index value representing the line-edge or line width roughness minus a change quantity due to noise. A bias due to noise included in the line-edge or line width roughness involves reproducibility of evaluation of a semiconductor evaluation device, namely, a degree of a distribution of the measured values of parameters for the purpose of evaluation. Thus, in order to evaluate the semiconductor evaluation device, a distribution of the edge point positions itself due to noise need be evaluated.

The problem with the method disclosed in non-patent literature 2 is that first, the method is very time consuming. First, two sets or more of image data of the same visual field must be acquired. According to non-patent literature 2, the image data need be processed statistically, and at least two sets of image data is required. In addition, in order to obtain a result of high reliability, measurement must be made at least five positions empirically. Since the image data need be added in the same visual field, position deviations contained in the image data should be corrected. When image data is acquired using the scanning electron microscope, the position of an examination specimen can deviate from the visual field of the image due to thermal vibration of the specimen or a drift of the stage. Correction of the position deviation is time consuming and requires the operator's experience and data processing is complicated. In addition, automation is difficult. A second problem is to damage to the specimen. In order to acquire data on a plurality of images, it is necessary to irradiate the specimen repeatedly with an electron beam (EB). Even when a beam irradiation time per unit image pickup operation is short, the whole EB radiation quantity increases by repeated irradiation.

As described above, the conventional method of calculating a bias component included in the line-edge or line width roughness needs two sets or more of image data and takes a long time for data processing. In addition, data analysis that requires skill need be made as a preprocess for the image data processing. Furthermore, the beam irradiation time for the specimen increases, thereby damaging the observation pattern possibly.

The problem to be solved by the present invention is to provide a method and apparatus for evaluating an index of line-edge or line width roughness present actually in an object to be observed, and a roughness component due to noise contained in a result of the observation from a piece of image obtained in a usual pattern observation, in a shorter time than in the past without losing substantially the same accuracy as in the conventional method.

SUMMARY OF THE INVENTION

Main five solving means for above-mentioned problems are disclosed herein and divided into two groups: ones using and not using Fourier's transform. In the following, their principles will be explained and any of the solving means described below uses any one of a change in a spectrum and a change in the level of random noise due to image averaging. In the following description, a standard deviation is used always as a roughness index. For simplifying purposes, line-edge roughness will be described and a similar method may apply to the line width roughness.

There is a theorem concerning a signal changing with time that the signal intensity per unit time is equal to integration of a power spectrum concerned. Applying this to the line-edge or line width roughness, it will be known that the square of standard deviation σ is equal to integration of the power spectrum of the roughness. In the following, the principle of the present invention will be described based on this property.

(1) First Method

The first method uses a property that the power spectral density of line-edge or line width roughness in high-frequency region is proportional to $f^{-2}$ where f is spatial frequency. In the function of power spectrum density distribution obtained directly from the original data provides a distribution in which the frequency characteristic of the high frequency area is not directly proportional to $f^{-2}$ because noise is included. In this case, averaging the original data will lead to reduction of the noise effect on the measured roughness. The effect of noise reduction increases as the number of averaging operations increases. For example, by performing the averaging operations an appropriate number of times, the power spectrum density distribution in the high frequency area will be directly proportional to $f^{-2}$. Thus, the point of the first method is that by increasing the number of averaging operations on one set of image data as the original data until the frequency (f) dependence of the power spectrum density in the high frequency area shows $f^{-2}$ property, the real spectrum component contained in the actually measured data is presumed, which is the point of the first method and will be described below in detail.

First, a relationship between edge roughness index to be acquired, averaged edge roughness index and free spectrum of the edge roughness (or power spectrum obtained by Fourier's transform of edge series data) will be described. For simplifying purposes, a unified unit of length to be used is nm. A direction extending along the line pattern is defined as a vertical or y-direction of the image, and a direction perpendicular to the vertical direction is defined as a horizontal or x-direction.

Observation data obtained by the microscope is made up of signal intensity profiles corresponding in number to the number of scanning lines. Each profile is an x-direction dependence of the detected secondary (or reflected) electron signal intensity in the microscope when the y-coordinate is fixed. The signal intensity I (x, y) of observation data (or subjected to no image processing) where the two-dimensional signal intensity distribution is composed of $x_{max}$ and $y_{max}$ data items in x and y directions, respectively, is given by $$I = f(x,y) \quad \text{Ex. 2}$$

where x is the value of an integer in a range of 1 through $x_{max}$ and y is the value of an integer in a range of 1 through $y_{max}$. Before image processing such as averaging, the profile comprises a function of x where y is regarded as a constant in Ex 2.

When the y-direction averaging process that is one of the simplest noise reducing processes is performed on the secondary electron intensity distribution, a resulting signal intensity is given by $$I = f'(x, y) = \frac{1}{S} \sum_{j=y-a}^{y+b} f(x, j) \quad \text{Ex. 3}$$

where S is the number of times of averaging parameters or operations, a and b each are (S−1)/2 when S is an odd number. When S is an even number, a=S/2, b=a−1 or b=S/2, and a=b−1. S=1 corresponds to performing no averaging process.

As will be known from Ex. 3, an averaged profile is obtained by averaging S unaveraged profiles. Thus, it is expected that the power of noise on the profile is reduced greatly, or to approximately 1/S, compared to that present when the profile was not averaged.

Thus, a basic method is deduced which when a roughness index is calculated, an operator who processes image data visually confirms a Fourier's spectrum averaged with parameter S while selecting a Fourier's spectrum averaged an appropriate number of times. The operator is required to increase the value of S until the noise of the spectrum decreases and the power spectrum density of a relatively high frequency area becomes directly proportional to $f^{-2}$, at which time the operator provides a roughness index using the value of S.

FIG. 4 illustrates a relationship between a spectrum including noise and a real spectrum. The both vertical and horizontal axes of the graph are in logarithmic scale. The slope of the power spectral density shown in FIG. 4 changes at a certain spatial frequency denoted as $f_0$. The spectral density is directly proportional to spatial frequency $f^{-2}$ in a higher frequency area than $f_0$. While this property has been observed in line patterns of various resists and said to be empirically correct, the physical or chemical meaning of $f_0$ has not yet been clarified. Approximately the position of $f_0$ is shown in FIG. 4. While in the real spectrum the $f^{-2}$ characteristic of the high frequency area appears, noise components such as shown dotted are superimposed on a spectrum obtained from observation data that has not been subjected to any image processing and the $f^{-2}$ characteristic is unclear. By increasing the value of the averaging parameter S, the superposed noise is restricted and a resulting spectrum changes from one with noise shown in FIG. 4 to a real spectrum, or the dotted area decreases.

In order to determine the end point of S without the operator's hand, a property is used in which the effect of noise elimination will be saturated when the number of averaging operations increases beyond a certain value. For example, if an algorithm is used which when a difference between the power spectral densities obtained in S and S+1 averaging operations is smaller than a certain threshold, determines that S or S+1 has reached the end of S, the end of S can be determined automatically. The power spectral density after the averaging operations of number S is calculated, thereby obtaining $\sigma_m$. More specifically, it is required that a frequency band of roughness that the operator desires to obtain is determined; the power spectral density after the averaging operations of number S is integrated in the frequency band; and then its square root is calculated.

Let $\sigma_0$ be a value obtained. Then, if $\sigma_e$ is calculated based on Ex. 1 from $\sigma_0$ and $\sigma_m$ obtained from the power spectral density acquired without being subjected the averaging operations, $\sigma_e$ is an index representing an extent of noise present when no averaging operations are performed. In the following $\sigma_m$ of Ex. 1 is regarded as a function of averaging parameter S as required and notated as $\sigma_m$ (S). For example, $\sigma_e$(1) represents $\sigma_e$ obtained when S=1 or when no averaging operations are performed.

(2) Second Method

There is a problem with the first method that information on roughness of a short period in the y direction, or fine roughness along the edge of the line pattern, may disappear due to averaging. FIG. 5 shows the power spectral densities of the measured roughness data before and after the averaging operations. The both vertical and horizontal axes of the graph are in logarithmic scale. Let Δy be an interval of electron beam scanning. Then, as the averaging parameter increase, the power spectrum of the roughness changes as shown in FIG. 5. Noise is superimposed on a high frequency area of the spectrum when no averaging operations are performed on the data. When the data is averaged with averaging parameter S, a roughness whose period is shorter than SΔy will be leveled out and then disappear. This influence will also be exerted on components having a longer period than SΔy and as a result, the intensities of components having a period shorter than 2SΔy will be reduced greatly. This can be easily confirmed by averaging a sinusoidal waveform having a period T. As a result, noise components is reduced in the spectrum obtained after the averaging operations and simultaneously the power spectrum intensity is greatly reduced in an area where the frequency is higher than 1/(2SΔy).

In order to obtain a real edge roughness index, the following should be made: First, a spectrum materially free from noise is obtained by averaging the original image data sufficiently (for example, a spectrum obtained after the averaging operations shown of the FIG. 5 graph). However, in this spectrum, a signal in a high frequency area where f≧1/(2SΔy) is not correct). In determining a value of the averaging parameter S for a sufficient averaging operation, the first method may be used. The frequency-dependence of a power spectrum in the high frequency area where the spatial frequency f is f≧1/(2SΔy) is predicted or extrapolated based on the shape of a spectrum of a part of an area close to the high frequency area where the spatial frequency f is f<1/(2SΔy). The following expression is used for a fitting curve to be used for extrapolation:

$$PSD(f) = A/f^2 \qquad \text{Ex. 4}$$

where f is the spatial frequency, and A is a proportional constant. That is, there is a property that the power spectral density (directly proportional to the square of a Fourier's amplitude) is inversely proportional to the square of the spatial frequency in the high frequency area. Data to be used for extrapolation purposes should be taken from a low frequency area where the spatial frequency f<1/(2SΔy) on the right side of a boundary point appearing in the power spectrum. That is, the operator specifies a frequency $f_1$ equal to, or higher than, $f_0$ and extrapolates, using averaged power spectrum data present between $f_1$ and f=1/(2SΔy).

FIG. 6 shows a graph of power spectrum density in which data in the high frequency area is compensated for by extrapolation. Both the vertical and horizontal axes of FIG. 6 are in logarithmic scale as same as in FIG. 4. In the graph of FIG. 6, a spectrum approximating to the real spectrum compared to the graph of FIG. 5 is obtained. In this approximating spectrum, a low frequency area for f<1/(2SΔy) indicates a spectrum obtained after the image data is averaged while a high frequency area for f≧1/(2SΔy) indicates predicted values.

In order to calculate a noise component quantity using the second method, a required frequency area band (or a hatched part+a dotted part of FIG. 6) is integrated on the spectrum of FIG. 6. The integrated value can be regarded as the square of $\sigma_0$.

As described above, the second solving method comprises calculating the hatched part of FIG. 6 by approximating a spectrum of the actually measured data, thereby calculating $\sigma_0$. Like the first solving method, an influence $\sigma_e$ (1) of noise can be calculated if $\sigma_0$ is known.

(3) Third Method

There are three problems with each of the first and second methods as follows. First, the operator must determine a value of a averaging parameter to sufficiently reduce noise. To this end, the operator needs skill. In order to achieve automation, examples of analysis of spectra obtained under various materials and conditions of observation must be formed as a database, which is presumed to be time consuming. A second problem is that data processing in Fourier's transform and analysis of a spectrum shape is time consuming. A third problem is that $2^n$ data items are needed to perform Fourier's transform at high speeds. If the number of data items is not equal to $2^n$, edge series data in a specified area must be interpolated/extrapolated so as to be $2^n$ data items, which is also time consuming. Thus, such calculation would invite an increase in the calculation time and hence the examination time as well as an increase in the capacity of memory. If software that performs such a complicated analysis is set on the examination device, a large part of the storage area of the device would be occupied, thereby imposing restrictions to other functions.

In summary, it is desirable that the calculations described concerning the first and second solving methods can be implemented easily (or without performing Fourier's transform if possible) on a CD-SEM.

In third, fourth and fifth methods to be described below, $\sigma_0$ is calculated using a statistic property that the intensity of random noise is reduced to 1/S by averaging. When $\sigma_0$ is calculated, an index $\sigma_e$ (1) of noise in the device that is not dependent on the averaging parameter can also be calculated.

For simplifying purposes, let L and Δy be the length of an examination area and an interval at which an edge point is extracted, respectively (it means that edge-point extraction interval is set to equal to electron beam scanning interval). All roughness index values obtained under these conditions will be discussed below. That is, when integration is discussed on a power spectrum, the integration range is assumed to be 1/L to 1/(2Δy).

Let $\sigma_e$ contained in data averaged with an averaging parameter S be $\sigma_e$ (S). Then the following relationship holds:

$$\sigma_e(S) = \sigma_e(1)/\sqrt{S} \qquad \text{Ex. 5}$$

This expression itself represents a well-known statistic property and is used in the present method.

A stream of this method will be summarized below. Let $\sigma_m$ (S) be the value of a line-edge roughness index obtained from the averaged data. First, a value of the line-edge roughness index, $\sigma_m$ (1), is calculated from data not subjected to the averaging processes. Then, the image is averaged to obtain a line-edge roughness index. Line-edge roughness index is preferably calculated for plurality of S values. Let $S_{min}$ and $S_{max}$ be a minimum value and a maximum one, respectively, of averaging parameters S to be used for the analysis. Then, we have a set of values $(S_1, \sigma_m(S_1)), (S_2, \sigma_m(S_2)), \ldots (S_N, \sigma_m(S_N))$ where $S_1=1$. Although described later, $S_{min}$ and $S_{max}$ must be set carefully.

In the third method, these data are simply fitted in Ex. 1. In this case, using Ex. 5, the following expression is given:

$$\sigma_m(S) = \sqrt{\sigma_0^2 + \{\sigma_e(S)\}^2} = \sqrt{\sigma_0^2 + \{\sigma_e(1)\}^2/S} \qquad \text{Ex. 6}$$

In fitting, $\sigma_0$ and $\sigma_e$ (1) are used as fitting parameters.

A value of $\sigma_0$ thus obtained is defined as a real roughness index value, which is the third solving method. This method corresponds to performing the first method, avoiding Fourier's transform. The square of $\sigma_m$ (S) obtained from data observed usually corresponds to an integrated value of a spectrum including noise in FIG. 4. A value of $\sigma_0^2$ to be obtained corresponds to integration of the real spectrum in FIG. 4 while integration of a dotted area is $\{\sigma_e(S)^2\}$. This corresponds to taking data by changing S and fitting the S-dependence of integration of the dotted area with $\{\sigma_e(1)^2/S\}$. There are two fitting parameters. Thus, for fitting purposes, at least two sets of values of measured data to be fitted are needed. That is, $N \geq 2$.

(4) Fourth Method

It should be noted in the third method that as explained in FIG. 5 and the description of the second method, when the value of S is large, high frequency components of the line-edge roughness are cut and not contained in the measured values. Assume now that when the value of the averaging parameter is S, noise is sufficiently reduced. FIG. 7 schematically illustrates a power spectrum in which noise is sufficiently reduced by S-averaging operation. A graph of FIG. 7 is plotted based on vertical and horizontal axes marked off in logarithms. In the spectra of resist pattern roughness reported so far, a maximum value of a frequency $f_0$ at a boundary point in the spectrum shape is 0.008 nm$^{-1}$. That is, the power spectrum density can be considered to be directly proportional to $f^{-2}$ in at least an area where f>0.008 nm$^{-1}$. The graph of FIG. 7 is drawn based on this fact and also shows a relationship in magnitude between that value, $1/(2S\Delta y)$ that is a minimum value of a frequency area where the power spectrum density is greatly reduced when the data is averaged with the averaging parameter S, and $1/(2S\Delta y)$ that is a limit of the frequency of the roughness discussed herein.

The first or third method corresponds to neglect of the presence of the FIG. 7 hatched area. Considering that the vertical axis of the graph is marked off in logarithms, a proportion of the whole roughness index that the hatched area of FIG. 7 occupies is small and when S is small, there is no problem with the first or third method. More specifically, when the length L of the examination area is 1 micron or more and the product of S and $\Delta y$ is 50 nm or less, the first or third method will suffice for the evaluation of the roughness. The reason for this is as follows: In many cases, many users desire to set L to a value of more than 1 micron to understand dispersion of the transistor performance. In this case, when the spectrum of the roughness of the resist observed so far is analyzed and the product of S and $\Delta y$ is 50 nm or less, the area of a hatched part of FIG. 7 to be observed by the averaging occupies 90% or more of the whole hatched area. That is, the value of $\sigma$ to be observed is 95% (or the square root of 90%) or more and it is considered that even when the influence of the hatched part is neglected, sufficiently accurate measurement is achieved.

Under the conditions where a percentage of the whole roughness index that the area of the hatched part of FIG. 7 occupies is relatively large, a quantity corresponding to the hatched part of FIG. 7 need be corrected for the roughness index to be obtained (in the second method, the correction quantity is presumed by assuming that the high frequency area spectrum is represented by an approximate curve). In a solving method to be described below, a correction term is added to Ex. 6 for correcting purposes. That is, $$\sigma_m(S) = \sqrt{\sigma_0^2 + \{\sigma_e(S)\}^2 - \{\sigma_{LOST}(S)\}^2} = \sqrt{\sigma_0^2 + \{\sigma_e(1)\}^2/S - \{\sigma_{LOST}(S)\}^2} \qquad \text{Ex. 7}$$

where the square of $\sigma_{LOST}(S)$ represents a dispersion calculated from the cut high frequency components and corresponds to the hatched part of FIG. 7. In order to fit a result of the measurement using this Ex. 7, the S-dependence of $\sigma_{LOST}$ (S) must be known beforehand. In the following, two methods, i.e., fourth and fifth solving methods, using Ex. 7 will be described.

First, the fourth method will be described. While described with reference to Ex. 4, a spatial frequency distribution of line-edge roughness that will be naturally generated has a property that the power spectral density is inversely proportional to the square of frequency $f^2$ in the high frequency area.

A lower limit $f_0$ of the high frequency area referred herein (or an area where the power spectral density is inversely proportional to the square of frequency f) depends on the resist material and a patterning process employed. (Hereinafter, the unit of frequency should be represented by nm$^{-1}$).

The power spectral density PSD (f) in an area where f>$f_0$ is obtained by integrating the hatched part of FIG. 7 and $\sigma_{LOST}$ (S) satisfies:

$$\sigma_{LOST}(S)^2 = 2A\Delta y(S-1) \qquad \text{Ex. 8}$$

Substituting this expression into Ex. 7, we have:

$$\sigma_m(S) = \sqrt{\sigma_0^2 + \{\sigma_e(1)\}^2/S - 2A\Delta y(S-1)} \qquad \text{Ex. 9}$$

The data measured need be fitted, using this expression with $\sigma_0$, $\sigma_e(1)$ and A as fitting parameters. In this case, three sets or more of measured values are needed. That is, $N \geq 3$ is required. S and $\Delta y$ must satisfy $2S\Delta y < 1/f_0$ nm where $f_0$ is a bending point on the spectrum mentioned above. Although its physical origin is not clear, it is confirmed in every resist pattern that $f_0$ is 0.008 nm$^{-1}$ or less. Thus, $S\Delta y$ need be set so that $2S\Delta y < 1/125(\text{nm}^{-1})$.

(5) Fifth Method

In this paragraph, another fitting method using Ex. 7 (or a fifth solving method) will be described. Since the number of fitting parameters is large in the fourth method, the value of A or its alternative variable is calculated beforehand in this method. This corresponds to advance calculation of information in the high frequency area. There are three kinds of methods of calculating the value of A or a corresponding quantity. In the following, each method will be described below.

Method 5-1

First, a first method of calculating the value of A or its corresponding quantity will be described. As described with reference to the fourth method, the high frequency area of the power spectrum of the roughness is represented by a simple function such as Ex. 4. Thus, it will be easily known that the dotted part of FIG. 7 is also represented easily by A $(1/f_1 - 2S\Delta y)$. Then, the image is averaged using $S_0$ as the averaging parameter value, thereby reducing noise sufficiently. Then, an examination area L is set to $1/f_0$ nm or less, thereby acquiring image data, and then line-edge roughness index $\sigma_A$ is calculated based on the image data. Of course, in this case length L along a line of the examination area must be shorter than the inverse of 0.008 nm$^{-1}$ or 125 nm because otherwise, the integration range would contain an area other than that where the spectrum is represented by Ex. 4 and cannot be expressed in a simple expression. Then, $$\sigma_A^2 = A(1/f_1 - 2S_0\Delta y) \qquad \text{Ex. 10}$$

is solved, thereby obtaining constant A, which is then substituted into Ex. 8. This fixes $\sigma_{LOST}$ (S) in Ex. 7, which can be written as:

$$\sigma_m(S) = \sqrt{\sigma_0^2 + \{\sigma_e(1)\}^2/S - 2\Delta y(S-1)\sigma_A^2/(1/f_1 - 2S_0\Delta y)} \qquad \text{Ex. 11}$$

using this expression, measured data $\sigma_m$ (S) should be fitted with $\sigma_0$ and $\sigma_e(1)$ as the fitting parameters.

As in the fourth method, expression $f_0 \leq f_1 < 1/(2S\Delta y)$ and further $f_0 \leq f_1 < 1/(2S_0 \Delta y)$ must hold. In many cases, $f_0 \ll 1/(2S_0 \Delta y)$. In such a case, $2S_0 \Delta y$ of the right side of Ex. 11 may be neglected.

In order to calculate the value of $\sigma_A$ correctly in performing this method, a plurality of examination areas should be set along the line-edge of the pattern, image data on these examination areas should be measured and then an averaged value of the squares of edge roughness indexes, $\sigma_A$, should be calculated. As the number of areas for measurement is larger, a better result is obtained. According to a rule of thumb, if the measurement is made until a total of lengths of the measurement areas amounts to approximately 2 microns and resulting values are averaged, dispersion will be reduced sufficiently. In order to calculate $\sigma_A$ accurately, $\sigma_A$ need not be measured actually each time in addition to the usual observation. This is because although an error involving $\sigma_A$ is $\sigma_{LOST}$ (S), this $\sigma_{LOST}$ (S) itself is not so large in usual observation, its influence on $\sigma_0$ and $\sigma_e$ (S) is very small.

Method 5-2

A second method (hereinafter referred to as method 5-2) of calculating the value of A or a corresponding variable will be described next. This method is substantially the same as method 5-1. In method 5-2, the value of A is calculated using the fourth method. First, an image of high magnification (or small $\Delta y$) where an image of an object appears is prepared and examination areas are set on an edge of the object appearing on the image. In the set examination areas, data series $\{\Delta x_i: \Delta x_1, \Delta x_2, \ldots\}$ and $\{\Delta w_i: \Delta w_1, \Delta w_2, \ldots\}$ of the edge roughness are calculated and then the obtained data serieses are processed statistically, thereby obtaining $\sigma_m$ and $3\sigma_m$ as the roughness bias indexes. In addition, the averaging parameter S is changed and the averaging process is performed on each data series with a respective one of different averaging parameters S to obtain a corresponding roughness bias index for a respective data series obtained with the respective one of the different parameters S. As described above, the S-dependability of the roughness bias index is calculated and A is calculated in the fitting process (where the number of fitting parameters is 3) using the fourth method using Ex. 9. By calculating A beforehand like this, a data series of the edge roughness obtained using any L can be analyzed in the fitting process (where since A is known already, the number of fitting parameters is only two; $\sigma_0$ and $\sigma_e$ (1)) using Ex. 9.

Any length L may be taken along the edge of the examination area when A is calculated, but it is preferably selected as long as possible under the conditions that the image is of a sufficiently high magnification. Roughness varies from place to place. Thus, when L is short, the values of A would vary Thus, preferably, the values of A are calculated and averaged in as many places as possible. It means that the fourth method is performed many times, that is, it needs times and skill. However, as L increases, the reliability of values of A to be calculated will increase and hence L should be increased preferably. According to the present method 5-2, the roughness index can be obtained with high accuracy compared to the method 5-1, and unlike method 5-1, there is no limit to the length L of the examination area.

Method 5-3

In order to obtain the value of A or a corresponding variable value in the fifth method, another method can be considered (hereinafter referred to as method 5-3). Also in the method 5-3, the fourth method is used to obtain the value of A. First, in order to obtain the value of A, an image of a small $\Delta y$ is prepared as in method 5-2. The S-dependence of the roughness value is calculated on a pattern edge of the prepared image. In this case, unlike method 5-2, a small examination area length L is taken. According to a rule of thumb, a maximum value of L is 125 nm and preferably 100 nm or less. Under these conditions, the whole frequency areas of roughness to be detected are in a high frequency area where the power spectral density conforms to Ex. 4. Thus, integration of Ex. 4 is the square of $\sigma_A$. That is, we obtain:

$$\sigma_A^2 = \int_{1/L}^{1/2\Delta y} A/f^2 \, df = A(L - 2\Delta y) \qquad \text{Ex. 12}$$

where L and $\Delta y$ are an examination area length and a scanning line interval, respectively, in the measurement for obtaining the value of A beforehand. By substituting the L and $\Delta y$ into Ex. 7, one of A and $\sigma_A$ can be erased. If, for example, A is erased, we obtain $$\sigma_{Am}(S) = \sqrt{\sigma_{A0}^2 \left\{1 - \frac{2\Delta y(S-1)}{L - 2\Delta y}\right\} + \frac{\{\sigma_e(1)\}^2}{S}} \qquad \text{Ex. 13}$$

where the value of $\sigma_A$ obtained after the averaging operations were performed with the averaging parameter S was expressed as $\sigma_{Am}$ (S), $\sigma_{A0}$ represents $\sigma_A$ free from the influence of noise, and $\sigma_e$ (1) the influence of noise on this image (for obtaining A or $\sigma_a$). In this case, $\sigma_{A0}$ need be obtained by fitting according to Ex. 13 and then substituted as a real $\sigma_A$ into Ex. 11. Note that since the value of L is small when $\sigma_A$ is calculated, $\sigma_{A0}$ are preferably measured in several places and fitted, thereby obtaining an averaged value.

Once $\sigma_A$ or A is calculated in any of the methods 5-1, 5-2 and 5-3, it can be used for analysis of patterns of the same design size created with the same materials in the same process. Among these three methods, method 5-1 that uses no fitting to obtain A or $\sigma_A$ requires a shortest calculation time. Method 5-2 provides high accuracy and requires the operator to do a smallest quantity of work. Thus, method 5-2 is suitable for automation of the analysis work. Method 5-3 has a merit that as the number of measurement places increases, the measurement accuracy improves greatly.

A maximum one of values of $f_0$ observed in various resist patterns so far is 0.008 nm$^{-1}$, which is preferably used as the value of $f_0$. For example, 125 nm is used as the value of L.

In the above, the third method using Ex. 6 and the fourth and fifth methods using Ex. 7 have been illustrated. In any of these methods, only one fitting operation is required and a Fourier's conversion process can be omitted which imposes a burden on the calculation unit compared to the first and second methods that performs the averaging operations with the plurality of averaging parameter values, thereby obtaining edge roughness. Use of the third-fifth methods allows an error $\sigma_e$ of roughness due to random noise to be quantified in a short time. In addition, a real roughness index value $\sigma_0$ can be calculated and hence high-accuracy roughness of high throughput can be measured.

In the above, the principle of the means for obtaining roughness indexes has been described in each of the first-fifth methods. Since the first or second method includes the step of observing a spectrum visually, it has a merit that the user can immediately notice the occurrence of roughness having a peculiar period due to the influence of a mask or a peripheral pattern. Thus, this method is suitable for analysis of the characteristics of line-edge roughness of a circuit pattern in the semiconductor manufacturing process and/or a study of development of devices. The third method is suitable for analysis of an image in which a long area along the edge is observed at very fine scanning intervals because the ratio of $\sigma_{LOST}(S)$ to the whole roughness is small. When a length along a line of the observation area is short or the scanning line intervals are large, a relative value of $\sigma_{LOST}(S)$ to roughness to be measured is large. Thus, correction is required. Accordingly, in such a case the fourth method in which accurate measurement is possible by correction is suitable. In addition, when the number of scanning lines is small or the magnification of a (y-) direction along the edge is low, the fourth method is suitable because in such a case, $\Delta y$ is large and a high frequency area on the spectrum is not observed, and hence the value of A cannot be obtained possibly in the fourth method in which the value of parameter A is fitted based only on the obtained data. If the fifth method in which $\sigma_A$ s obtained beforehand from an image observed with higher magnification is used, A is determined with high accuracy and $\sigma_0$ and $\sigma_e$ can be calculated accurately.

In the third, fourth and fifth methods, the results can vary depending on whether which area involving the actually measured values (or range of values of S) should be used for fitting purposes. There are two reasons: first, an edge detection error will occur which cannot be described only with $\sigma_e$ when S is too small, and second, when S is too large, the power spectrum cannot be described in Ex. 4. In order to determine a minimum value $S_{min}$ of S, the position of an edge point detected should be viewed during measurement and whether the position is appropriate or not should be confirmed. According to experience of the inventors, it is known that when a stay time per pixel of an observing beam (or a total time for which the observing beam was applied to one pixel) is approximately 2 μs or less, $S_{min}$ should be 3 or more. The maximum value $S_{max}$ should be selected such that a value of $2 \times S_{max} \times \Delta y$ is smaller than $1/f_0$. It can also be said empirically that $S_{max}$ should be selected such that $2 \times S_{max} \times \Delta y$ equals 125 nm or less.

When the fifth method is employed for the reason that $\Delta y$ is large as described above, the obtained roughness index value corresponds to a value obtained by sampling the edge at intervals of $\Delta y$. However, even with this interval the sampling density can be insufficient. In this case, high frequency parts of the power spectrum that cannot be detected at the sample intervals of $\Delta y$ can be calculated using $\sigma_A$ and added, thereby calculating a value corresponding to the roughness measured at very small sample intervals.

By expressing the aforementioned algorithm with software, implementing the software on information processing means such as a computer and using the software for analysis of image data obtained from appropriate image data acquiring means, the problem of the present invention will be solved. While data obtained from the scanning electron microscope is used often as the image data, the present invention is applicable to analysis of all image data such as transmission electron microscope images and X-ray images.

The high-accuracy pattern shape evaluating method and apparatus according to the present invention has the function of quantifying the influence of random noise on line-edge roughness when a fine pattern is observed with the scanning microscope and calculating a value closer to real edge roughness by subtracting the quantified noise value from the measured value. In addition, these calculations can be performed based on a single sheet of observation image. In this calculation, the user need not perform a complicated operation such as parameter setting. Thus, high-accuracy roughness measurement can be performed easily in a short time even from an image of high noise, thereby allowing the finer pattern shape to be evaluated. This produces an advantageous effect that the examination time is reduced and deformation/damage of the pattern in observation is restricted, advantageously. Thus, in fine working, development of materials and processes and screening can be performed accurately with a low damage. Even in mass production process, high-accuracy examination is achieved, thereby improving productivity.

The influence of random noise quantified can be used as a noise index of the device. Using this result, it can be determined whether the observation conditions are good or not (for example, whether the microscope is in focus). By measuring and preserving this index over a long time, a long-time stability of the device performance can be evaluated, thereby improving productivity.

Other objects, features and advantages of the invention will become apparent from the following description of the embodiments of the invention taken in conjunction with the accompanying drawings.

BRIEF DESCRIPTION OF THE DRAWINGS

FIG. 12 is a flowchart indicative of detailed procedures of step 1101 of calculating a roughness index from image data, which step will be performed in Embodiments 3-5.

DETAILED DESCRIPTION OF THE INVENTION

Embodiment 1

This embodiment illustrates application of the first method to a CD-SEM, which will be described next.

Figure 18:
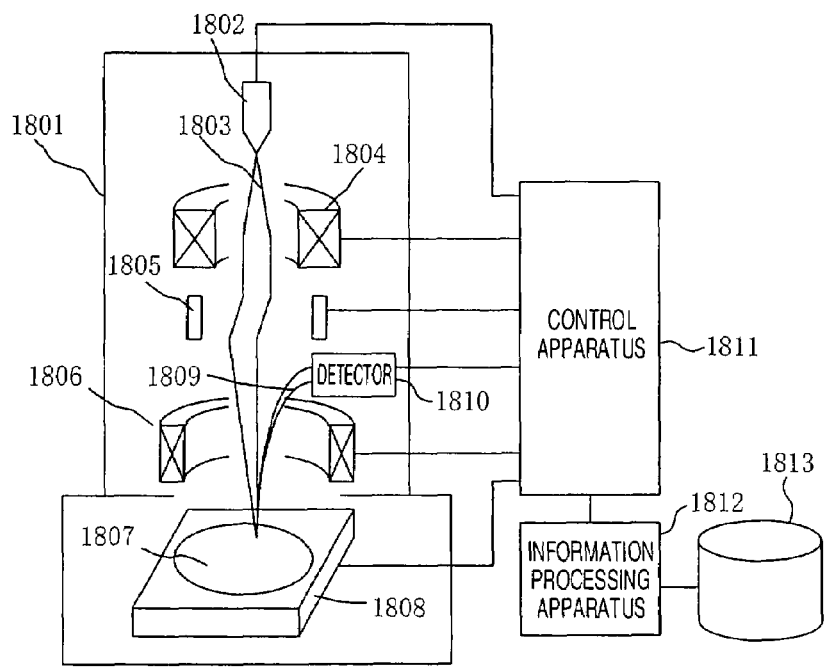
FIG. 18 schematically illustrates the structure of an examination device used in Embodiment 4.

FIG. 18 schematically illustrates a hardware structure of the CD-SEM used in this embodiment. The CD-SEM mainly comprises housing 1801 of a scanning electron beam microscope that comprises an optoelectronic (or SEM) column and a specimen chamber, a control system 1811 for the microscope and information processor 1812. Information processor 1812 is connected to a data storage device 1813 that stores an obtained scanned electronic image and CAD data necessary for analyzing purposes. Data storage device 1813 can be provided within information processor 1812. Although not shown, information processor 1812 comprises an information input terminal that an operator of CD-SEM inputs information necessary for data processing to information processor 1812 and an image display means that displays a scanned electronic image acquired. A specified information input terminal may include a keyboard, a mouth or an GUI picture that will be displayed on the image display means.

The optoelectronic column comprises electron beam gun 1802, focusing lens 1804, deflector 1805, objective lens 1806, and detector 1810. The specimen chamber comprises stage 1808 on which examination wafer 1807 is placed as an object to be examined. Secondary electrons 1809 produced from wafer 1807 by irradiation of electron beam 1803 from electron beam gun 1802 are detected by detector 1810, and converted by control system 1811 to digital data, which is then transferred to information processor 1812, thereby producing image data to be used for analyzing purposes.

In this embodiment, image data of the object was acquired in pattern observation using the scanning electron microscope provided on the CD-SEM. The acquired image data is then preserved in data storage device 1813. After the observation, the information input terminal is operated to analyze image data, thereby obtaining a roughness index.

Figure 8:
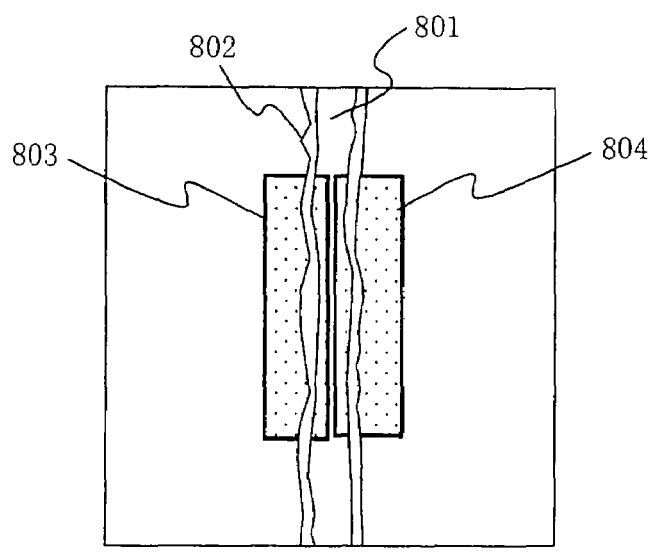
FIG. 8 illustrates a rectangle indicative of observation image data and an examination area appearing on an examination device display picture in Embodiments 1, 2 and 3 of the present invention.

First, an image of a pattern from which the roughness index is to be acquired was displayed on the monitor picture. FIG. 8 schematically illustrates a SEM image of the pattern analyzed in this embodiment. The image of FIG. 8 was obtained by averaging secondary-electron signal intensities obtained in 32 scanning operations performed on an ArF resist line pattern from an upper left corner to a lower right corner of the visual field. The number of pixels of the observation image is 1500 in vertical and horizontal directions with one side of each pixel corresponding to 1 nm. That is, the length of the observation image in the visual field was 1.5 μm in each of vertical and horizontal directions. For emphasizing purposes, in FIG. 8 a flat area in which the secondary electron intensity is low is illustrated as a dotted area and an area indicative of the vicinity of an edge of the line pattern is illustrated by a white part. Examination areas 803 and 804 are set in the vicinity of the center of the FIG. 8 image. Examination areas 803 and 804 are set by the operator of the CD-SEM and in this embodiment each of the examination areas comprises a rectangular area of 1024 by 50 pixels. This area was placed on an edge (or area 802 indicative of the vicinity of the edge) to be analyzed by manipulating the mouth. At this time the examination areas are denoted by 803 and 804.

When examination areas 803 and 804 are set, a request to input set values necessary for extracting a data series of edge roughness is displayed on the GUI picture. The device user sets information necessary for extracting the data series, which includes a sampling interval for data extraction in the y-direction, a noise reducing parameter in the x-direction, an averaging parameter S in the y-direction, etc. Instead of the sampling interval for data extraction in the y-direction, the number of detection points may be set. When input of the required information is terminated, confirming icons such as "Detection area setting has ended", "Data series extraction setting has ended", etc. are displayed on the GUI picture. When the device user clicks any one of the icons, a task that extracts a data series of the edge roughness in the area starts to be executed.

When this task starts, the CD-SEM information processor calculates a profile corresponding to a y-coordinate of a sampling position from pixel data in each of examination areas 803 and 804 in accordance with the set data extraction start point and set sampling interval and then calculates x-coordinate data indicative of the edge point from the profile. This process is shifted and performed one after another in accordance with the sampling interval in the y-direction and finally data series $\{\Delta x_i: \Delta x_1, \Delta x_2, \ldots\}$ or $\{\Delta w_i: \Delta w_1, \Delta w_2, \ldots\}$ of the edge roughness are obtained in each examination areas 803 and 804.

In order to confirm the influence of the averaging operation visually, in this embodiment S was set to 1 first. As a y-coordinate at which the data extraction started, a y-coordinate corresponding to a lower side of each of the examination areas 803 and 804 was set, and the sampling interval was set to 1 nm. Edge points in the examination area were extracted at intervals of 1 nm from image data where S=1, or unaveraged image data, thereby extracting 1024 point positions $(x_1, y_1), \ldots, (x_i, y_i), \ldots (x_{1024}, Y_{1024})$. An averaged line width of the pattern calculated from the data series obtained was 110 nm.

Then, by approximating an arrangement of the obtained points with the following straight line, the values of α and β as the fitting parameters were calculated:

$$x = \alpha y + \beta \qquad \text{Ex. 14}$$

An $i^{th}$ deviation $\Delta x_i$ of an $i^{th}$ edge point from the straight line was calculated in accordance with:

$$\Delta x_i = x_i - (\alpha y_i + \beta) \qquad \text{Ex. 15}$$

In this way, edge roughness series $\{\Delta x_i\}$ was produced, which is defined as a series of edge roughness obtained at an averaging parameter S=1.

When the task of extracting the data series of edge roughness is terminated, a power spectrum obtained by Fourier's transform of the edge roughness series of 1024 data items is displayed on the GUI picture. When the power spectrum is displayed, a request to ask the user whether or not the averaging parameter S need be reset is displayed on the GUI picture. When the user inputs an answer that the resetting of S is needed to the information processor, the request to reset S is displayed on the GUI picture. The device user inputs a new S value in accordance with instructions of the GUI. In this case, the information processor may have software that resets a noise reducing parameter in the x-direction in addition to the averaging parameter S. When an answer that resetting of S is not required is inputted to the information processor, the analysis ends at this point of time.

In the present embodiment, the horizontal noise reducing parameter remains fixed to 3 and each time S is incremented by one, the y-direction averaging operation is performed on the original image, thereby obtaining an edge roughness series from the image, and power spectrums obtained one after another by Fourier's transform are displayed on the same graph.

Figure 9:
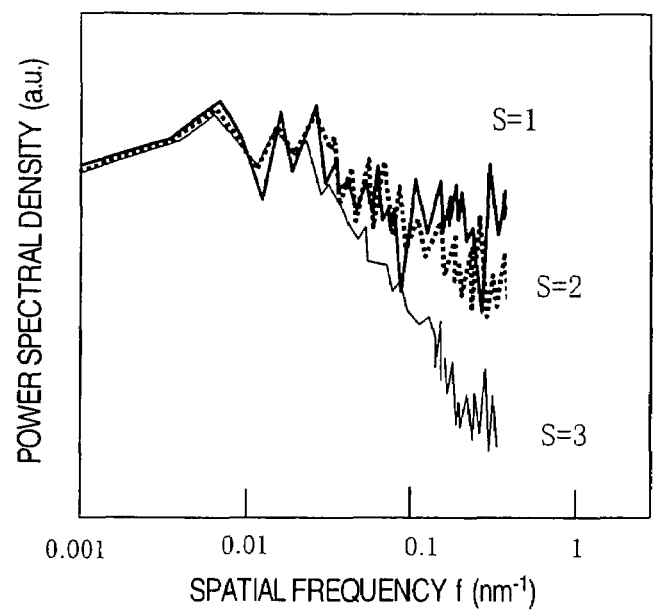
FIG. 9 illustrates a power spectrum of edge roughness obtained in Embodiment 1.

FIG. 9 shows a state of the display picture obtained by repeating the resetting of averaging parameter S until S=3. Appearance of an image in which the power spectrum density of the high frequency area at S=3 is directly proportional to $1/f^2$ was confirmed visually. Since even when S was 4 or more, noise (due to roughness in the high frequency area) remained materially unchanged, it was determined that S=3 was appropriate.

Edge points were extracted using image data on which the averaging operation was repeated until S=3 based on that result, a power spectrum was obtained from 1024 data items and their σ was calculated as 1.20 nm. In order to obtain a profile at the sampling position of y=i after the averaging operation when S>2, profiles at y values of from i+1−S/2 to i+S/2 when S is an even number are averaged, and profiles at y values of from i−(S−1)/2 to i+(S−1)/2 when S is an odd number are averaged. Thus, information on image data present outside the set examination areas actually will mix. When a difference between the number of pixels of the original image in the y-direction and the number of pixels of a y-direction length of the set area is smaller than S, an error is displayed. A line-edge roughness index in 1 μm of the examination area length was recorded as 1.20 nm. The definition may be changed so as to employ 3σ instead of σ.

It is known that when roughness indexes are obtained by fixing the averaging parameter to 3 and then the respective roughness indexes are obtained for subsequent line pattern images of the same observation conditions, the influence of noise will decrease. Thus, the examination was performed so.

In the past, S=2 was employed uniformly in all the examinations without optimizing the value of S. Thus, although values containing much noise were obtained when the number of additions of secondary electron intensities was small, these values were used for pattern examination. Thus, even a pattern in which the roughness is not so large was regarded as having a bad (or very rough) shape and the lithography step was performed over again. In contrast, by using the present method that includes changing S, displaying the spectrum and then confirming a situation in which noise is reduced, high-accuracy roughness measurement is achieved and productivity of the semiconductor manufacturing process or apparatus improves.

While in the present embodiment the edge roughness was described, a roughness in the line width may be similarly analyzed. In this case, an examination area need be set also on another edge of the same line when the examination areas are set. This additional examination area is denoted by 804 in FIG. 8. Then, 1024×2 point positions on the left and right edges are obtained and denoted by $(x_{L1}, y_{L1})$, . . . $(x_{Li}, y_{Li})$, . . . $(x_{L1024}, y_{L1024})$ and $(x_{R1}, y_{R1})$, . . . $(x_{Ri}, y_{Ri})$, . . . $(x_{R1024}, y_{R1024})$, respectively. Now, a local line width $w_i$ is defined as follows:

$$W_i = \chi_{Ri} - \chi_{Li}$$ Ex. 16

If this set $\{w_i\}$ is replaced with $\{\Delta x_i\}$, subjected to Fourier' transform and then analyzed, line width roughness will be discussed instead.

Embodiment 2

The present embodiment relates to application of the second method to the CD-SEM, which will be described next. In order to describe the present embodiment, FIGS. 8, 9 and 10 will be used. The CD-SEM used in this embodiment has exactly the same hardware structure as the first embodiment. Thus, in the following, the description of Embodiment 1 concerning FIG. 18 will be used as requested.

FIG. 8 schematically illustrates a SEM image of a pattern analyzed in the embodiment. FIG. 9 illustrates a display picture obtained by repeating the resetting of averaging parameter S until S=3. A process ranging from the setting of examination areas 803 and 804 of FIG. 8 to acquisition of the power spectrum of FIG. 9 is exactly the same as that of Embodiment 1.

As described in Embodiment 1, advent of the circumstances in which the power spectrum density of the high frequency area was directly proportional to $1/f^2$ when S=3 was confirmed visually. On the other hand, however, the power spectrum density of an area where f>0.15 is extremely reduced in the graph at S=3 because since S is large, short-period components are erased. In order to cope with situation, this area is approximated with a function directly proportional to $1/f^2$.

When in the present embodiment the CD-SEM operator inputs an answer that the resetting of S is not needed to the information processor, a message requesting to ask whether or not data missing in the high-frequency area due to the averaging operations should be compensated for is displayed on the GUI picture. When the operator inputs that compensation for the high frequency area data is needed to the information processor, the GUI picture displays a message requesting to input designation of a data area to produce an approximate curve in the high frequency area. The operator then sets data to set the approximate function, or upper and lower limits of the frequency area for the power spectrum, in answer to the message. The operator sets the upper and lower limits for an appropriate range in the x-axis direction for the power spectrum at S=3 shown in FIG. 9 by moving a pointer such as a cursor. In the present embodiment, the approximate curve calculation area was set for 0.03<f<0.15.

Figure 10:
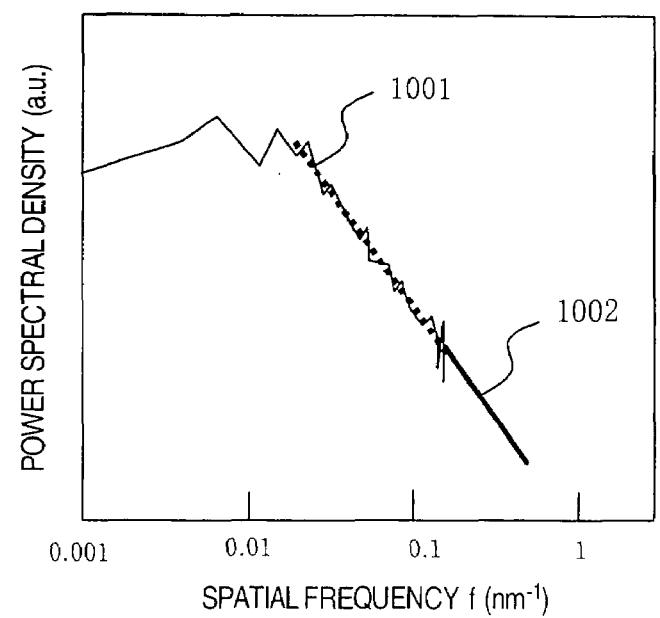
FIG. 10 illustrates a power spectrum of edge roughness obtained in Embodiment 2 and an approximate curve.

When inputting the approximate function calculation area is terminated, information processor 1812 provided in the CD-SEM calculates a function approximating to the function of Ex. 4 by using data on the power spectrum in the set frequency area, calculating the value of A as the fitting parameter, and hence providing an approximate function. FIG. 10 schematically illustrates a picture on which the approximate function obtained is displayed superimposed on the power spectrum and the high frequency area from which data is missing due to the averaging operations is extrapolated. The approximate function obtained is represented by broken line 1001 in FIG. 10. This function is extended into an area where f>0.15 with the extended part shown by thick sold line 1002. In the area where data is missing or f>0.15, extrapolated values obtained from the approximate function are used for the spectrum data. That is, in f≦0.15 nm$^{-1}$ and f>0.15 nm$^{-1}$ areas, the spectrum obtained from the measured values, and solid line 1002 were used as the spectra parts obtained when noise was reduced sufficiently.

Then, this spectrum was integrated, thereby obtaining a value corresponding to the square of roughness index σ. As a result, σ was 1.22 nm.

This invention produces the same merits as described in Embodiment 1, and furthermore, σ can be measured more accurately than in the first embodiment.

Embodiment 3

Figure 11:
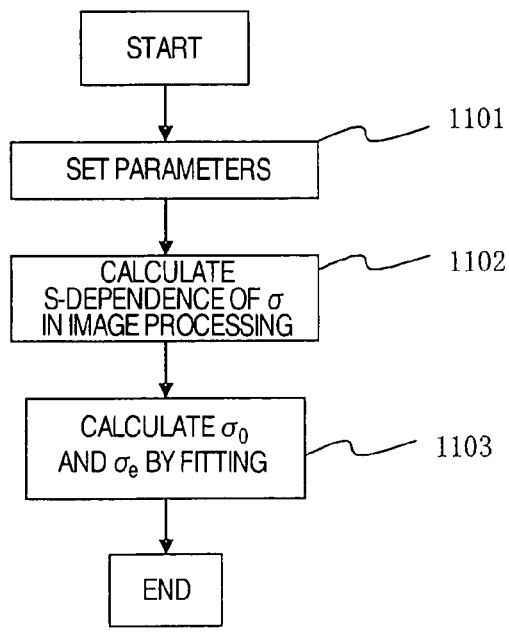
FIG. 11 is a flowchart indicative of a process of calculating and analyzing a roughness index from image data that will be performed in Embodiments 3, 4 and 5 of the invention.
Figure 13:
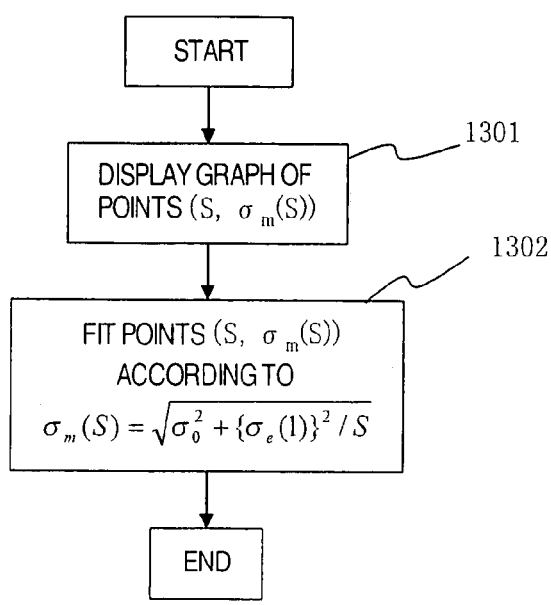
FIG. 13 is a flowchart indicative of the details of step 1102 in Embodiment 3 analyzing a roughness index obtained from the image data.
Figure 14:
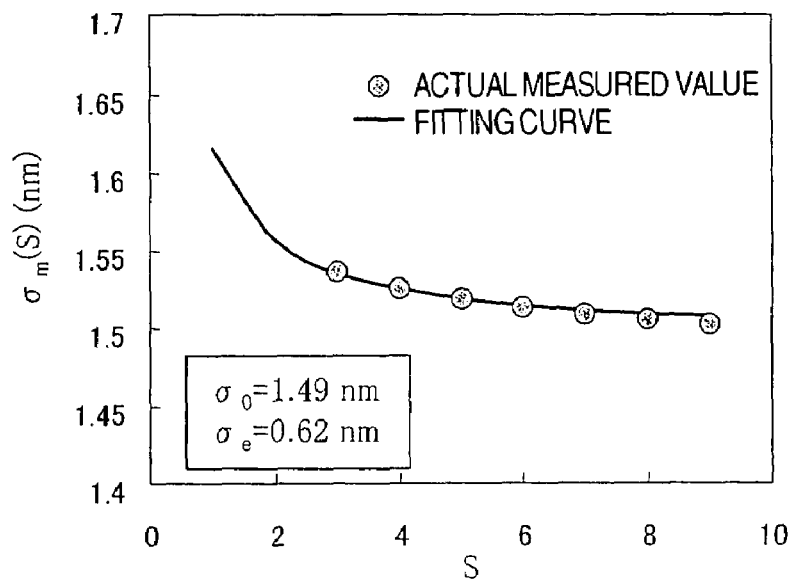
FIG. 14 schematically illustrates a display of a result of analysis obtained in Embodiment 3.

The present embodiment relates to application of the third method described in "Summary of the Invention" to the CD-SEM, which will be described next. The image data analysis method which will be described in the present embodiment comprises obtaining an index of roughness and an index of random noise occurring in the image without performing Fourier' transform from data used to calculate the roughness in Embodiment 1. In the description of the present embodiment, FIGS. 8, 11-14 will be used. FIG. 8 schematically illustrates a SEM image of a pattern analyzed in the present embodiment. FIG. 11 is a flowchart of a calculation process performed in the present embodiment. FIGS. 12 and 13 are flowcharts each representing a part of the process of FIG. 11. FIG. 14 shows roughness indexes obtained from the image and a graph of a fitting curve as a result of the analysis. The CD-SEM used in the present embodiment is exactly the same structure as used in Embodiment 1. Thus, in the following description, the description of Embodiment 1 concerning FIG. 18 will be used as required.

Also in the present embodiment, a pattern is observed and its image data is preserved as in Embodiment 1 and 2. After the observation, the computer terminal is operated to analyze the image data, thereby obtaining roughness indexes.

First, an image of a pattern from which the roughness indexes are to be obtained is called from data storage device 1813 and displayed on the monitor picture. The present embodiment uses the same observation image as Embodiments 1 and 2. The number of pixels in the visual field is 1500 in each of the vertical and horizontal directions with one side of a pixel corresponding to 1 nm.

Next, examination areas were set. Examination areas each 1024 pixels long and 50 across were displayed at substantially the center of the image and then placed on an area that contains an edge (or an area 802 close to the edge) to be analyzed by mouth operation. In this way, examination areas 803 and 804 were set. FIG. 8 schematically illustrates a pattern image on which examination areas 803 and 804 are set on an examination image called from data storage area 1813. While in the following, analysis of examination area 803 will be described, analysis in examination area 804 will also be performed using the same method.

Then, referring to FIG. 11 the whole flow of an analysis algorithm to be used in the present embodiment will be described. The image data analysis to be performed in the CD-SEM of this embodiment is mainly composed of step 1101 of setting parameters and a range of data necessary for acquiring a roughness index to be obtained from an examination image, step 1102 of obtaining data on the averaging parameter S-dependency of an roughness index $\sigma_m$ to be obtained from the examination image, and step 1103 of fitting the data and calculating a contribution $\sigma_0$ of roughness present in the pattern and a roughness index bias value $\sigma_e$ due to the influence of random noise.

When the examination areas are set on the examination image displayed on the monitor picture, the analysis flow passes to step 1201, thereby displaying a window on which parameters necessary for the analysis will be set on a monitor picture. The parameters set in this step are divided into parameters to define an edge from a two-dimensional gray image and averaging parameters in the respective x- and y-directions. The former includes a start point (or y-coordinate) where the edge roughness is extracted, and a sampling interval in the y-direction at which edge data is extracted. The latter includes a noise reducing parameter w in the x-direction, a minimum value $S_{min}$ and a maximum value $S_{max}$ of averaging parameter S in the y-direction. In the present embodiment, a y-coordinate of a lower side of the examination area 803 was set as the start point of edge roughness extraction. Furthermore, 1 nm was set as the sampling interval in the y-direction, 3 was set to $S_{min}$, 9 to $S_{max}$ and 3 to w, respectively.

When the parameters are set, the flow passes to step 1102. FIG. 12 illustrates a more detailed flow of step 1102. Then, the details of a flow of producing data on the averaging parameter-dependency of the roughness index will be described, using FIG. 12.

When the respective parameters are set in step 1101 and the processor user then clicks an ENTER button displayed on the GUI picture, information processor 1811 of FIG. 18 smoothes an x-direction signal using the value of w set for pixels in examination area 803.

When the x-direction signals are smoothed, the flow passes to step 1202 in which the value of averaging parameter S is initialized or set to 3.

The flow then passes to step 1203 in which information processor 1811 performs a pixel operation on image data in examination area 803, performs a y-direction averaging operation on the examination area at the set parameter value. Then the flow passes to step 1204 to extract edge points in the examination area where the averaging process was performed. In the present embodiment, edge points are extracted in units of a pixel at intervals of 1 nm in the vertical or y-direction according to the set values. The flow then passes to step 1205 where the values of coordinates of 1024 points $(x_1, y_1), \ldots (x_{1024}, y_{1024})$ obtained in the previous step were approximated with Ex. 13 using the method of Embodiment 1, thereby producing an edge roughness series $\{\Delta x_i: \Delta x_1, \Delta x_2, \ldots\}$ according to the definition of Ex. 14.

Then, the flow passes to step 1206 where a standard deviation $\sigma_m$ (S) on 1024 data items contained in the edge roughness series (S) was calculated, and $\sigma_m$ (S) and the value of S were stored in pair in data storage device 1813. That is, data sets $((S_{min}, \sigma_m (S_{min})), ((S_{min}+1, \sigma_m (S_{min}+1)), \ldots, ((S_{max}, \sigma_m (S_{max}))$ were stored in data storage device 1813.

Then, the flow passes to step 1207 where information processor 1811 determines whether the averaging process has been completed based on the value of S. If S is smaller than $S_{max}$, the flow passes to step 1208 where the value of S is incremented by one and again the flow passes to step 1203. A looping operation of steps 1203-1206 is repeated until S equals $S_{max}$ in step 1207, at which time the looping operation is terminated.

In the above steps, values cm (S) of from S=$S_{min}$ (in this embodiment, 3) to $S_{max}$, (in the present embodiment, 9) are obtained from the examination image, thereby terminating the flow of producing data on the averaging parameter-dependency of the roughness index shown in step 1102 of FIG. 11.

Next, the data processing flow passes to step 1103 which is described in detail in FIG. 13, and the following description is given, using FIG. 13.

When production of data on the averaging parameter dependency of the roughness index is terminated, the flow passes to step 1301 where sets of results $(S_{min}, \sigma_m (S_{min}))$, $(S_{min}+1 \ \sigma_m (S_{min}+1)), \ldots, (S_{max}, \sigma_m (S_{max}))$ obtained are displayed as a graph on the display picture. Then, the flow passes to step 1302 where these points are fitted on assumption that these points follow Ex. 6 and then the values of $\sigma_0$ and $\sigma_e$ (1) as the parameters are calculated. Note in the present embodiment that $\sigma_e$ (1) was used as $\sigma_e$. Simultaneously, a fitting curve (obtained by substituting the parameter values obtained by the fitting into Ex. 6) is plotted on the graph. FIG. 14 shows this graph. In the present embodiment, $\sigma_0=1.49$ nm and $\sigma_e(1)=0.62$ nm. The results were displayed on the graph and the fitting process was terminated.

Thus, the process of FIG. 11 was terminated and $\sigma_0$ and $\sigma_e$ were obtained. The value $\sigma_0$ thus obtained was used as an index representing a merit of the shape of the observed pattern and $\sigma_e$ was recorded as an index representing a degree of noise occurring in the examination device. Since these two parameters are obtained accurately and rapidly, the efficiency of pattern shape management and hence productivity improve. The performance of the examination device is capable of being monitored over a long time, thereby improving productivity.

While in the present embodiment the edge roughness was calculated, line width roughness can be used as an index instead of the line-edge roughness. In that case, as described at the end of Embodiment 1, right and left edge points of the line pattern are extracted, the distance between the right and left edge points having the same y-coordinate is calculated at each of y=1 through 1024 and then analysis similar to that used for the edge roughness is required on the respective distances calculated.

In the present embodiment, no free spectrum is involved, and hence the calculation is simple and does not take much time. Since the function of the conventional length measuring SEM is used, any new calculation program need not be implemented into the examination device and the memory of the examination device is not pressured either. Since there is no process for determining an optimal S value using a visual observation, there is a merit that analysis can be easily automated compared to the techniques of Embodiments 1 and 2.

As described above, by implementing software that embodies the algorithms shown in FIGS. 11-13 on the information processor for the CD-SEM, thereby performing image data analysis, the CD-SEM produces excellent advantageous effects described above.

Embodiment 4

The present embodiment relates to application of the fourth method described in "Summary of the Invention" to the CD-SEM, thereby acquiring an image in line while analyzing the roughness, which will be described next. An object to be inspected is a semiconductor wafer having a resist layer formed after being subjected to lithography. Length measurement and roughness analysis were performed.

Figure 20:
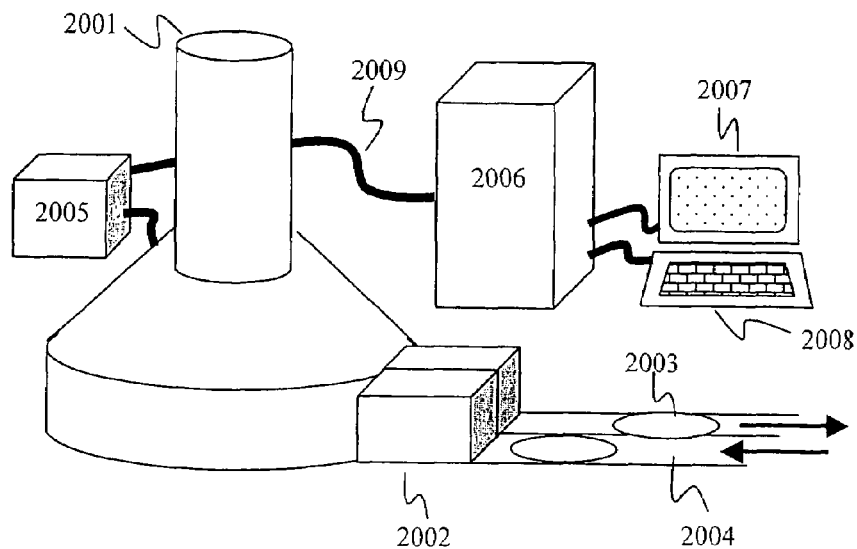
FIG. 20 schematically illustrates the structure of an in-line length measurement/roughness analysis system.

FIG. 20 illustrates the structure of an in-line roughness analysis system using the CD-SEM. Reference numeral 2001 denotes a SEM housing that houses a photoelectric device for acquiring a SEM image such as an optical system for electron beam irradiation, a secondary electron detector and or a specimen stage. The inside of the SEM housing is evacuated so as to maintain a high evacuated state. Reference numeral 2002 denotes a load lock chamber that acts as a spare vacuum chamber in which an examination wafer conveyed by a wafer conveyance system 2004 is temporarily stored before being conveyed into the SEM housing. Also, when the wafer is carried out of the SEM housing after the length measurement and image acquisition are terminated, the wafer is returned to the conveyance system through load lock chamber 2002. FIG. 20 illustrates a CD-SEM system with two separate load lock chambers into and out of which the wafer is conveyed. Although not shown, wafer conveyance system 2004 is connected to a wafer stocker such that history information on a wafer conveyed into SEM housing 2001 (for example, lot information) is transferred every moment to information processor 2006.

Reference numeral 2005 denotes a SEM control system that controls the respective components of the SEM including, for example, various lenses that compose the op to electric system and a drive voltage for the electron gun and/or a quantity of movement of the specimen stage. Information processor 2006 analyzes acquired image data. Thus, information processor 2006 includes a memory on which various analysis software are loaded, an arithmetic device that executes the software and/or a large-capacity storage that stores the acquired data. The large-capacity storage may be provided outside of information processor 2006. For example, a dedicated server for storage of image information may be provided so as to be connected to information processor 2006. Reference numeral 2007 denotes a monitor that displays an SEM image of a wafer acquired in SEM housing 2001 and a result of analysis performed by information processor 2006. Various numeral values necessary for execution of the analysis by information processor 2006 are set by information input means 2008 connected to information processor 2006. SEM housing 2001, SEM control system 2005 and information processor 2006 are connected through signal transmission cables 2009. For example, an image signal indicative of an examination specimen acquired by the secondary electron detector provided within SEM housing 2001 is transmitted via SEM control system 2005 to information processor 2006.

Then, an image data acquiring process will be described. A wafer subjected to a lithography step is carried into SEM housing 2001 through load lock chamber 2002. Information on the examination wafer carried into SEM housing 2001 is stored as an examination recipe already within information processor 2006. When the processor user starts up the system, or each time the history information on the examination wafer carried into SEM housing 2001 changes, the recipe is called through monitor 2007 and information input means 2008, and then various parameters necessary for roughness analysis are set. When these parameters have been set, wafer 2003 is placed on the stage within SEM housing 2001, and then image data is acquired.

Figure 19:
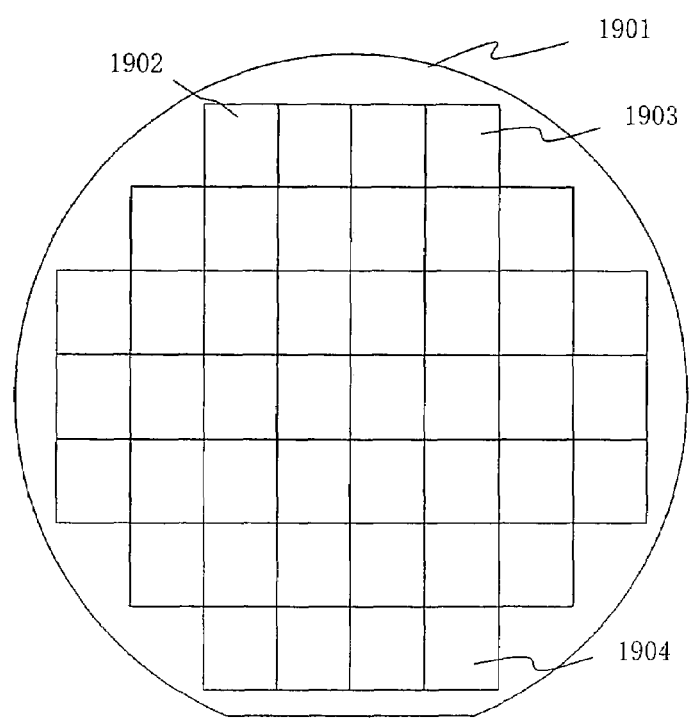
FIG. 19 schematically illustrates a chip layout of wafer examined in embodiment 4.

FIG. 19 illustrates layout of chips, whose roughness analysis will be performed, on the examination wafer. For all or 44 chips on the wafer, line patterns of ArF resists 5·m long×100 nm wide present at the same relative coordinates on the respective chips are to be inspected. Examination starts with chip 1902, proceeds to the right and then reaches the right end of the uppermost chip. Then, examination shifts to the right end chip of a row immediately below the uppermost row and then shifts to the left. Finally, examination reaches to chip 1904, thereby terminating the examination on the single wafer. When image data of each chip for analysis is acquired, the position of the specimen stage and the position of electron beam irradiation are controlled such that substantially the central position of the examination pattern within each chip is the center of the visual field. Areas of the respective chips having substantially the same coordinates and area and size are scanned by the electron beam, and secondary electron signals are detected. These detected signals are transmitted along with information on a specimen stage drive signal and an electron beam scanning signal to information processor 2006, converted to image data and then displayed as an examine pattern image on the monitor picture. An index (such as an identifier) to discriminate each chip from other is added to a respective of all the chips on the wafer. Acquired image data of each chip is stored along with its index in corresponding relationship into the storage of information processor 2006.

A process of analysis of the acquired image data will be described next. FIG. 11 is a flowchart indicative of the process of data analysis to be executed by the CD-SEM in the present embodiment. Note that in the present embodiment all parameters to be set in step 1101 are already registered in an examination recipe stored in the storage. Thus, information processor 2006 reads out parameters and analyzes the data as required. When the flow passes to the data analysis step after image data acquiring step, an image of the examination area acquired is displayed on the monitor picture. In the case of the present embodiment, the displayed pattern image comprises 2500 pixels long by 2500 across with one side of a pixel corresponding to 1 nm. This image was obtained by averaging secondary electron signal intensities that were obtained in 16 scanning operations each performed from an upper left corner to a lower right corner of the visual field. The reason why the 16 scanning operations were employed is to reduce damage to the pattern. However, this increased noise on the observation image.

First, an examination area is set automatically. Substantially the same process as described with reference to embodiments 1-3 is performed by information processor 2006. In the present embodiment, the examination area corresponds to 2000 pixels long and 60 pixels across.

When the examination area is set, the analysis step shown in FIG. 11 is performed automatically by information processor 2006. Also in this case, parameters to be set in the analysis are read out from the examination recipe and set automatically. In the present embodiment, the y-coordinate of a lower side of the examination area was set as a start point of edge roughness extraction; 1 nm as a sampling interval in the y-direction; 3 as $S_{min}$; 20 as $S_{max}$; and 3 as w. Next, $\sigma_m(S)$ data producing step 1102 of FIG. 11 is automatically executed. FIG. 12 illustrates the detailed flow of step 1102 whose description will be omitted because it was described in detail in Embodiment 3. A difference between Embodiment 3 and the present embodiment is only that the flow of FIG. 12 is executed automatically by the processor. Since the number of pixels in the y-direction in the examination area is 2000, the number of series data items indicative of the edge roughness obtained finally is 2000. In the above process, values $\sigma_m(S)$ involving from S=3 to S=20 were obtained.

Figure 15:
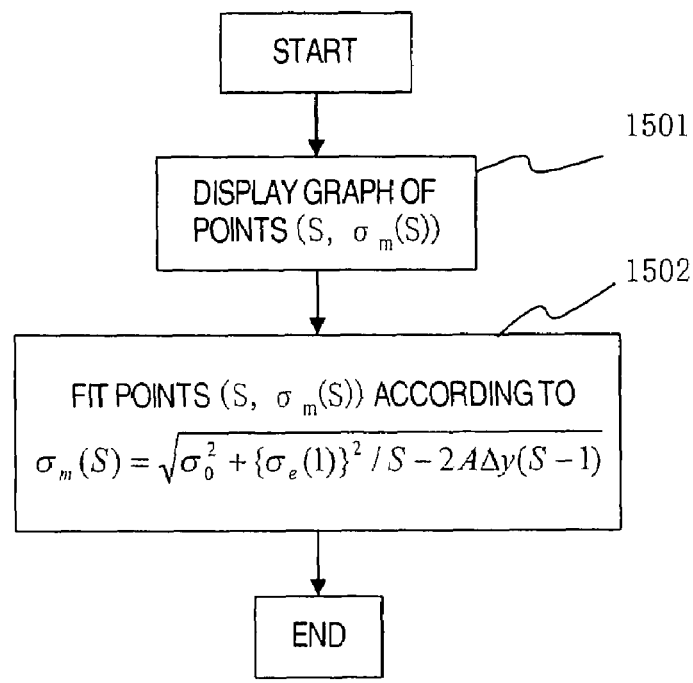
FIG. 15 is a flowchart indicative of the details of step 1102 in Embodiment 4 analyzing a roughness index obtained from the image data.

Then, the flow passes to step 1103 that calculates $\sigma_0$ and roughness index bias value $\sigma_e$. FIG. 15 illustrates a flow of step 1103 in detail. Description will be made below, using FIG. 15.

First, in step 1501, sets of results $\{(S_i, \sigma_m(S_i))\}$: $\{(S_{min}, \sigma_m(S_{min}))\}$, $\{(S_{min}+1, \sigma_m(S_{min}+1))\}$, ..., $\{(S_{max}+1, \sigma_m(S_{max}+1))\}$ obtained are displayed as a graph on the monitor.

Figure 16:
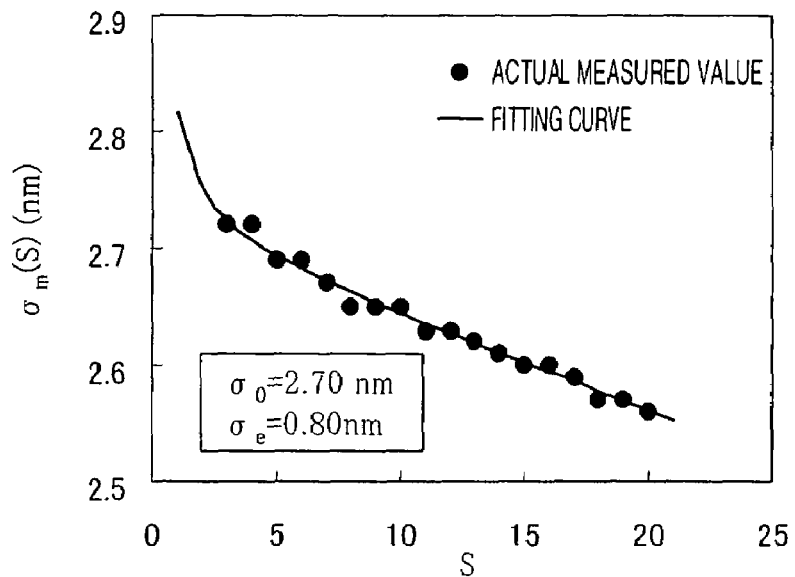
FIG. 16 schematically illustrates a display of a result of analysis obtained in Embodiment 4.

Then, the flow passes to step 1502 where fitting is performed on assumption that these points on the graph conform to Ex. 9. Fitting parameters are $\sigma_0$, $\sigma_e(1)$ and A. The least squares method was used as a fitting algorithm, thereby calculating values of parameters describing $\sigma_m(S)$ obtained from the acquired image. In this case, $\sigma_e(1)$ was used as $\sigma_e$. When $\sigma_0$, $\sigma_e$ and a fitting curve (obtained by substituting the values of parameters obtained as a result of the fitting into Ex. 9) are calculated, the obtained numerical values and fitting curve are displayed superimposed on a graph of $\{(S_i, \sigma_m(S_i))\}$ where i=min−max}. FIG. 16 shows this graph. In the present embodiment, with a chip having an $i^{th}$ index, results $\sigma_0$=21.70 nm and $\sigma_e$=0.80 nm were obtained. Thus, the process of FIG. 11 is terminated, and $\sigma_0$ and $\sigma_e$ for a chip having that index were calculated.

The process for obtaining $\sigma_0$ and $\sigma_e$ described just above was performed on a respective one of all the chips on the wafer of FIGS. 19 and 44 measured values were obtained for each chip. A list of values $\sigma_0$ and $\sigma_e$ on the respective chips was stored as examination records in information processor 2006. A calculated averaged value of the values $\sigma_0$ of all the chips (in the present embodiment, 44) was stored as typical roughness values of wafer in information processor 2006, and an averaged value of the roughness index $\sigma_e$ of all the chips was also stored as an index indicative of the state of the information processor 2006 on the examination date in information processor 2006.

The calculation of the edge roughness indexes is as shown above, and acceptance or rejection of the process performed on the wafer can be made using the calculated $\sigma_0$ and $\sigma_e$. In the following, determination of acceptance or rejection of a wafer using the whole chip average value of $\sigma$ will be described. In the present embodiment a criterion of $\sigma_0$ for accepting a wafer before the examination has been determined. The content of the criterion was that the average value of $\sigma_0$ was 2.50 nm or less and four of 44 examined chips should have $\sigma_0$ equal to, or larger than, 3.00 nm. This content was obtained as the requirements for maintaining 70% or more of yield by performing simulation of transistor performance and productivity. The criterion for acceptance has been stored as an examination recipe in the storage of information processor 2006. When the processor user sets an analysis sequence so as to determine acceptance or rejection of wafers, the examination recipe is read out and acceptance or rejection is determined. An average value of roughness indexes $\sigma_0$ of wafers examined in the present embodiment was 2.50 nm and determined as acceptable.

In the prior art, very much noise is contained in an image acquired with a small averaged number of 16 operations in the present embodiment and the averaged value of roughness indexes $\sigma_0$ obtained greatly tends to be calculated as a larger one than the real one. For example, in the processing of a wafer used in the present embodiment, the averaged value of roughness indexes $\sigma_0$ calculated in the past was 3-4 nm and many unacceptable wafers were produced. The unacceptable wafers are sent to a reproducing process in which the resist is separated from the wafer, cleaned and then a resulting wafer is again subjected to the lithography process. By using the present invention, a roughness close to the real value is measurable and it has been fined that the wafers determined to be unacceptable so far are acceptable actually. Thus, productivity in the manufacturing process improves.

Since the line-edge roughness analysis method of this embodiment needs no Fourier's transform, calculation is simple and can be made at high speeds. Thus, the present invention is especially suitable for an analysis system that requires a high throughput such as a roughness analysis in line. Since the present embodiment uses the function of a conventional length measuring SEM, no new calculation program need be implemented on the examination device and no memory of the examination device is pressured either. In addition, since contribution of high frequency components to the roughness that cannot be detected due to noise reduction has been corrected and hence the accuracy is high.

The method of this embodiment is suitable for analysis of an image acquired at high magnification because when data points obtained in the actual measurement are fitted in the present method, results of enhanced reliability are obtained as the number of data points used for fitting purposes increases.

Figure 1:
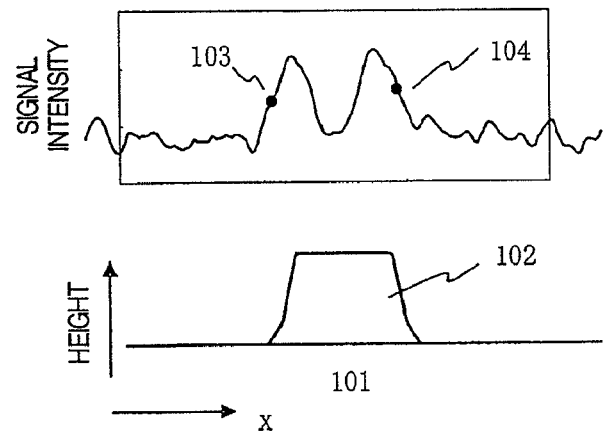
FIG. 1 schematically illustrates a relationship between the x-direction dependability of a secondary electron signal intensity or profile and a cross-section of an actual pattern.
Figure 2:
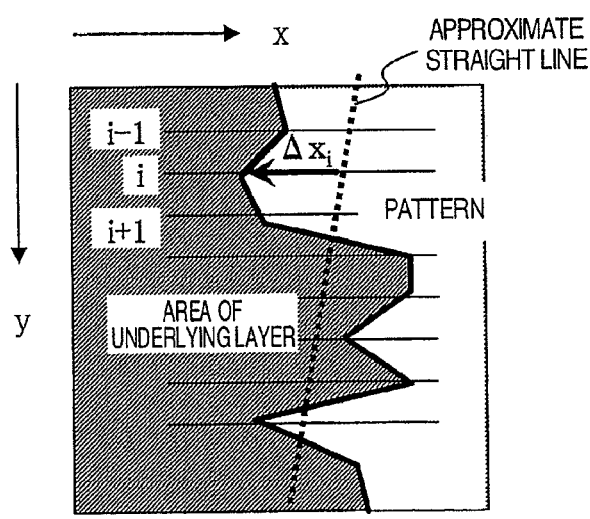
FIG. 2 schematically illustrates a relationship between a schematic view of a SEM image in the vicinity of a line pattern edge and edge roughness $\Delta x_i$.
Figure 3:
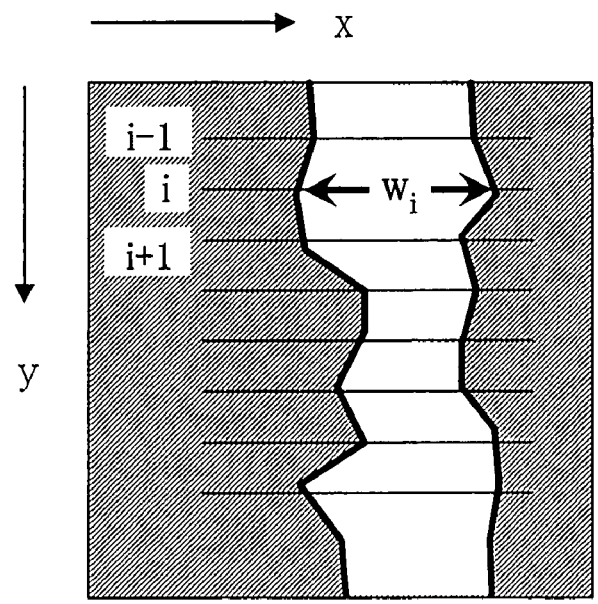
FIG. 3 schematically illustrates a relationship between schematic view of a SEM image of a line pattern edge and line width roughness $\Delta w_i$.
Figure 4:
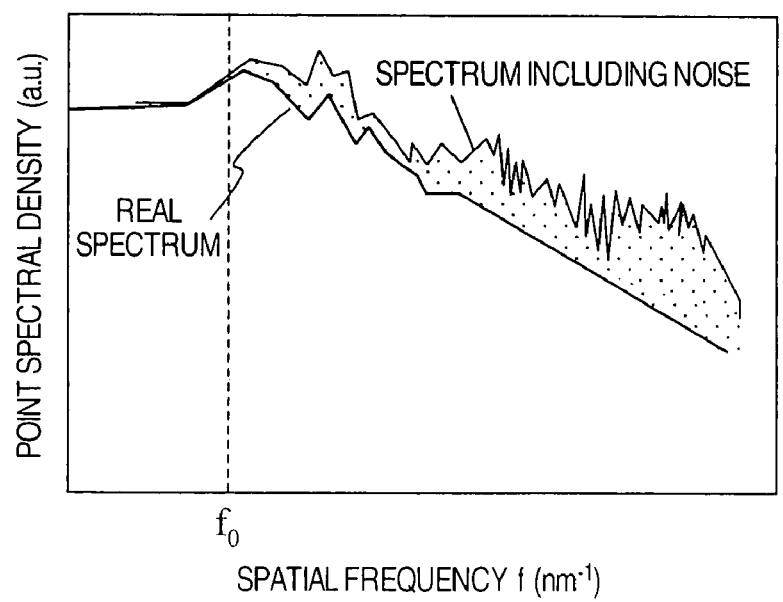
FIG. 4 is a schematic diagram of a power spectrum of real edge roughness that illustrates the influence of random noise on the power spectrum.
Figure 5:
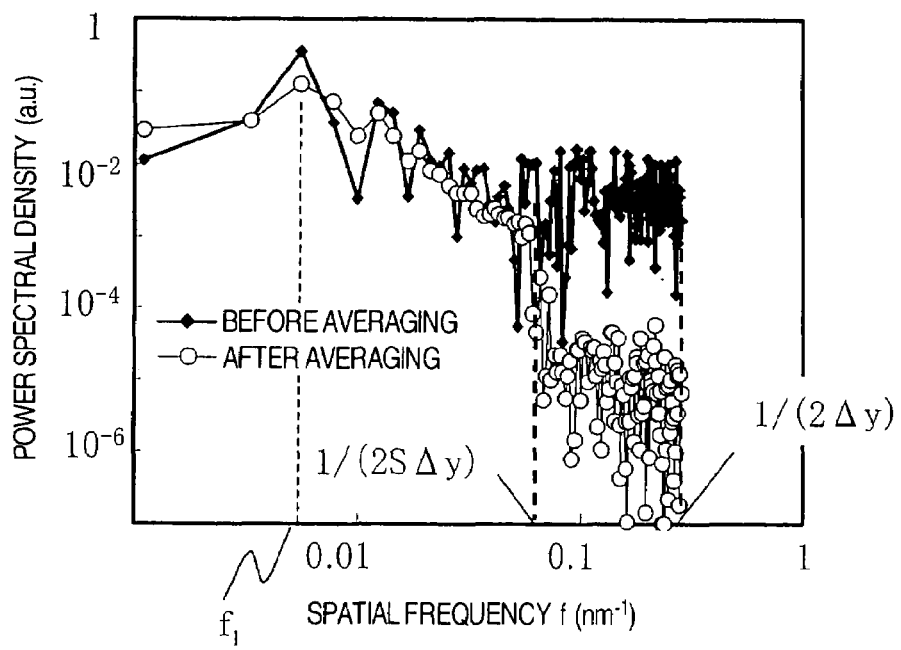
FIG. 5 is a schematic diagram of a power spectrum of edge roughness that illustrates the influence of image data averaging operation in a y-direction on the power spectrum.
Figure 6:
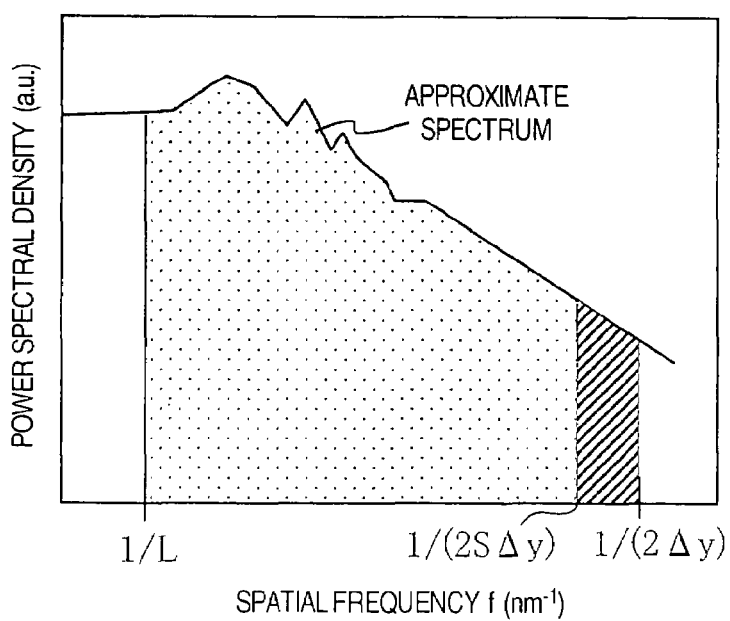
FIG. 6 illustrates a relationship between approximate power spectrum of edge roughness and roughness index calculated from the power spectrum.
Figure 7:
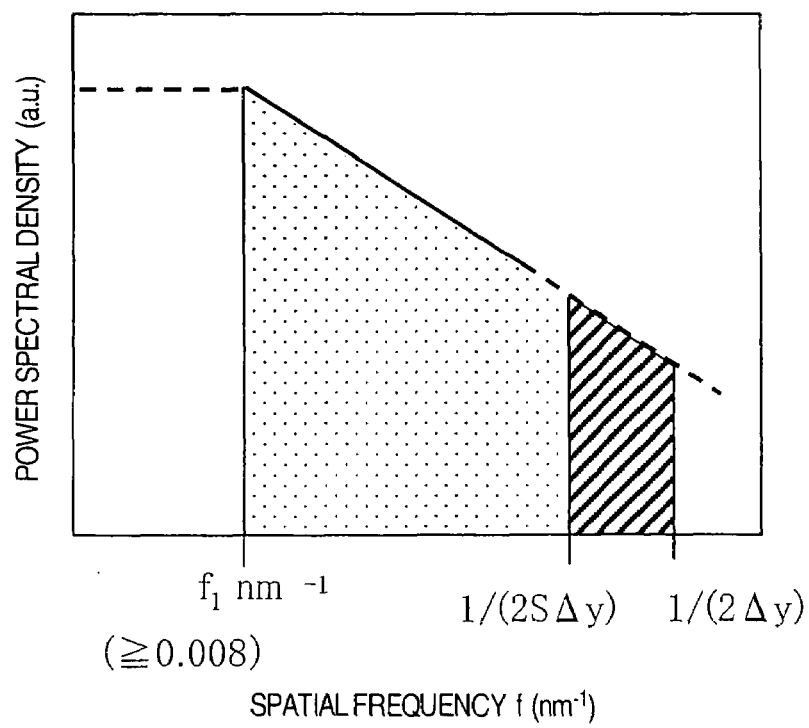
FIG. 7 illustrates a relationship between a value of roughness index obtained from the averaged data and a roughness component not included in the index value due to the averaging.

Increasing the number of data corresponds to increasing $S_{max}$. However, as described in the paragraph next to Ex. 4, a usable value of S has a limit because if S is large, a maximum period of the roughness components to be lost due to the averaging operations becomes larger than $1/f_0$ (that is, the left end of the hatched part of FIG. 7 shifts further to the left from the left end of the dotted part) and Ex. 8 does not hold. Thus, when the scanning line interval Δy is, for example, 10 nm, $S_{max}$ is 6 and only six measured data items can be used to obtain three fitting parameters. If Δy is 2 nm, 30 or more data items may be used for fitting purposes. Thus, the present method is suitable for analysis of a small Δy image or a high-magnification image.

While in the above description the observation and measurement of an image are illustrated as performed simultaneously, all images to be analyzed may be acquired and then roughness may be measured collectively. In this case, the images are temporarily stored in the storage of information processor 2006. In measurement, various parameter are set using monitor 2007 and information input means 2008 and then the same analysis as mentioned in the previous examples is performed.

As described above, since the roughness indexes are obtained accurately and rapidly, the efficiency of pattern shape management and productivity improved. By monitoring the value of $\sigma_e$ as an index of the examination device performance over a long time, productivity was improved.

While in the present embodiment the edge roughness was calculated, the line width roughness may be employed as an index instead of the line-edge roughness. In this case, as described at the end of Embodiment 1 the right and left edge points of the life pattern are extracted, distances each between right and left edge points having the same y-coordinate need be sequentially calculated from y=1 to y=2000 as a line width roughness series, and then analyzed likewise as in the edge roughness. While in the present embodiment the composition of the in-line measurement has been illustrated, this method is applicable to the off-line measurement, of course.

Embodiment 5

The present embodiment relates to application of the 5-2 method described in "Summary of the Invention" to the CD-SEM, thereby acquiring an image in line while performing roughness analysis, which will be described next. An object to be examined is a semiconductor wafer on which a resist layer was formed after being subjected to the lithography process. The length measurement and roughness analysis were performed. For analyzing purposes, the system structure of FIG. 20 was used which was the same composition as that of Embodiment 4. Since the details of the system composition of Embodiment 4 have been already described, and further description of the system of FIG. 20 will be omitted. The analysis flow of the present embodiment passes basically along FIG. 11. The present embodiment is different from the other embodiments in that the former has an algorithm that calculates $\sigma_0$ and $\sigma_e$, and beforehand calculates fitting parameter A appearing in the algorithm. Next, a process to be performed before the flowchart of FIG. 11 will be described.

When the system starts up or each time history information on an examination wafer that is carried into SEM housing 2001 changes, the processor user calls the recipe through monitor 2007 and information input means 2008, and then sets an area for acquiring a parameter A calculating image, an area in which length measurement and roughness analysis are performed, and various parameters necessary for the roughness analysis. The examination recipe cooperate with CAD data on the examination wafer, thereby setting an image area on the CAD data. Thus, in the present embodiment, information processor 2006 is connected to an external server that has stored the CAD data (not shown).

Figure 21:
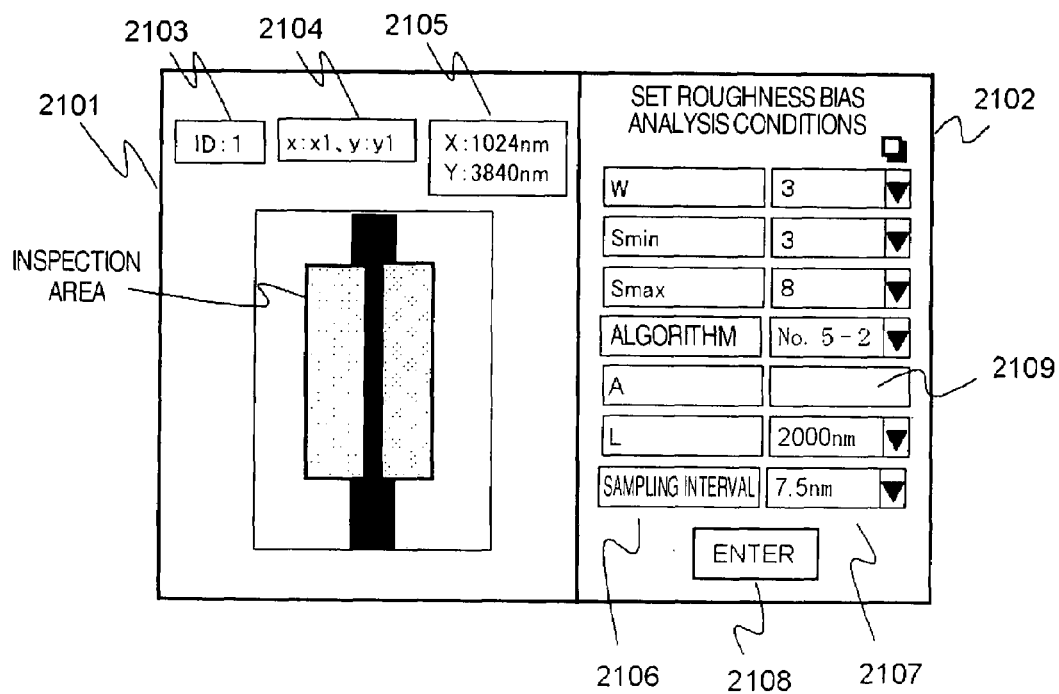
FIG. 21 illustrates an examination recipe picture for in-line measurement of Embodiment 5.

FIG. 21 illustrates one example of a display picture for the examination recipe of this embodiment. CAD display 2101 that displays a CAD image of an area where the roughness analysis is performed actually composes the left half of the display picture. In the CAD image of FIG. 21, an area painted black appearing below a dotted rectangle corresponds to an actual wiring pattern. CAD display 2101 displays an identifier box 2103 that indicates a management number of an examination wafer, a coordinate information box 2101 indicative of a part of the wafer corresponding to the present displayed CAD image, and a visual-field size display box 2105 that indicates how large the visual field of the present displayed CAD image is in each of the x- and y-directions.

Setting unit 2102 for a roughness analysis parameter is displayed on the right part of the display picture. Parameter setting unit 2102 has a set parameter display box 2106 indicative of various set parameters for roughness analysis. The processor user selects preferred numerical values from pull down menu 2107 corresponding to the respective set items and inputs them. The roughness analysis parameters to be set on the setting picture of FIG. 21 include, for example, x-direction averaging parameter w, and minimum and maximum values $S_{min}$ and $S_{max}$ of y-direction averaging parameter S.

Figure 22:
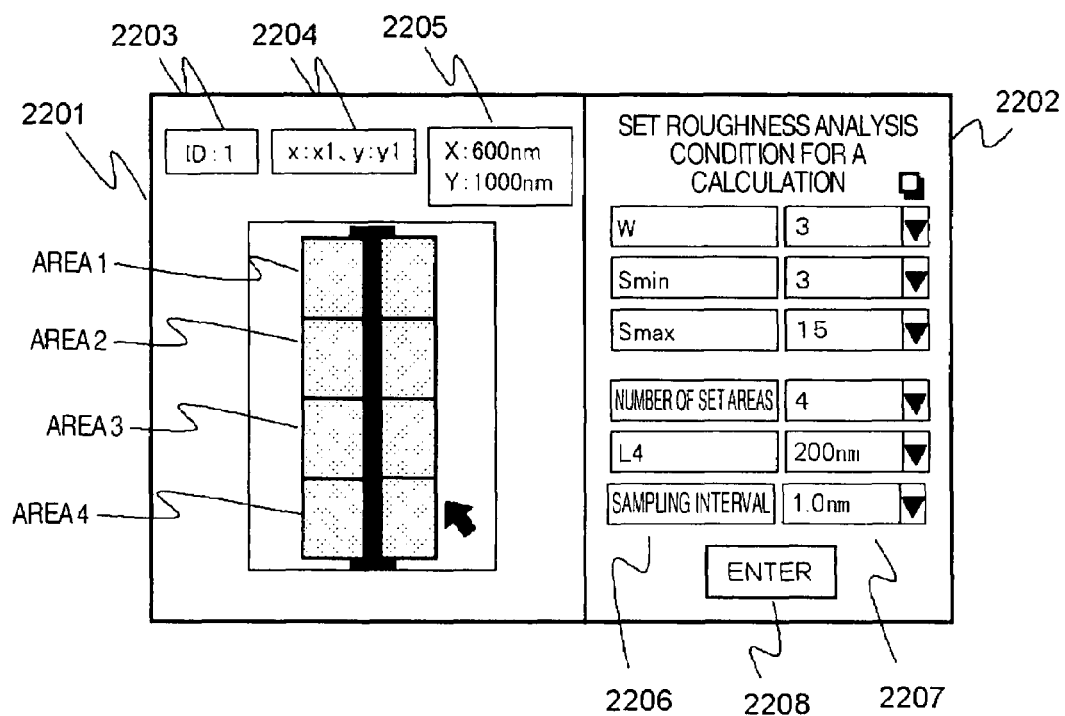
FIG. 22 illustrates a screen for designating a picture region for calculating parameter A on an examination recipe.

Now, when No. 5-2 is selected as an identifier of the algorithm that is used for roughness analysis, the set picture of FIG. 21 is switched to that of FIG. 22. The No. 5-2 algorithm corresponds to method 5-2. This is because with NO. 5-2, parameter A need be determined before the steps of calculating $\sigma_0$ and $\sigma_e$ are performed. The set picture of FIG. 22 is for setting areas from which spare images for calculating A are acquired. As shown in FIG. 22, elements 2201-2205 composing a part of the window are the same items as 2101-2105. The set picture of FIG. 22 is different from that of FIG. 21 in the number of set areas for determining A, length Ln of each set area where n varies depending on the number of set areas, and data sampling interval in each set area. The areas for acquiring the spare images are indicated by coordinates default set in the processor or set arbitrarily by the information processor or its user. In the present embodiment, the spare image acquiring areas were set for calculation of parameter A in the vicinity of an area approximately 5 μm above an area for calculating $\sigma_0$ and $\sigma_e$ to be set on the FIG. 21 set picture. When the spare-image acquiring area are set, a CAD image displayed when the picture switches from FIG. 21 to FIG. 22 is scrolled upward appropriately and the display magnification is further increased, thereby switching the CAD image displayed on the picture. While in the present embodiment it was arranged that the areas for acquiring the spare images do not overlap with that for acquiring an image where the roughness analysis is performed, both areas may coincide. However, note that when both do not coincide, there is an advantage that damage caused by the electron beam irradiation to the specimen will be reduced. While in the present embodiment the number of set examination areas was illustrated as 4, it may generally be more or less than 4. Note that the number of examination areas increases, the accuracy of A to be calculated improves. In order to calculate A accurately, image data acquired at as fine sampling intervals as possible is used preferably. Thus, as the spare images, images acquired under higher magnification conditions than the images for roughness analysis are used preferably.

When the processor user inputs the number of set areas for determining A, rectangles corresponding in number to the set areas are displayed superimposed on a CAD image displayed on CAD data display 2201 (see areas 1-4 of FIG. 22). A y-direction length Ln of each area and a length obtained by dividing the y-direction length of the visual filed of the displayed CAD image evenly by the number of set areas are default set. Argument n for L is one of natural numbers 1-4 corresponding to areas 1-4 in the present embodiment. Similarly, even in the x-direction, a default-set length is allocated to a line-edge on the CAD image. While the y-direction lengths of the respective area are set to the same length in default, but may be set to ones changing depending on the histories of the wafers examined. In this case, the processor user manipulates a pointer indicated by an arrow in FIG. 21, thereby changing the size of each of areas 1-4. When setting of each area is terminated, the processor user sets a sampling interval. In FIG. 22, the same sampling interval of 1.0 nm is set for areas 1-4, but the sampling interval may be changed for each area. When all the parameters have been set, the user clicks ENTER button 2308, thereby terminating inputting data to the set picture of FIG. 22. In order to operate the system actually, other conditions including ones for setting the optoelectronic system need be set, but their description will be omitted in the embodiment. Actually, the other conditions are set using a separate setting picture different from that of FIG. 21.

When ENTER button 2208 is clicked, wafer 2003 is placed on the stage within SEM housing 2001, thereby acquiring an actual image of an area of the wafer corresponding to the CAD image shown in FIG. 22. In order to acquire the image, a logic address on the CAD data need align with a physical address on the wafer, but its description will be omitted. Each of areas 1-4 where the image data were acquired in this process is 400 pixels long by 100 pixel across with one side of a pixel being 7.5 nm, as set in FIG. 21.

Image data for setting parameter A was acquired for each of areas 1-4 set in FIG. 22. By changing averaging parameter S in the vertical direction of the image sequentially from 3 to 15, edge roughness indexes $\sigma_{Am}$ (S) were calculated. These results were fitted using Ex. 9, or the fourth method, and then the values of A were calculated. To this end, the values of A were calculated for the four respective set areas 1-4 and their averaged value was employed newly as A, which was 5.2 nm. This value of A was then stored in the storage of information processor 2006 and also captured into the examination recipe corresponding to the examination specimen. Note that when a previous calculated A value can be used in the roughness analysis, the step of acquiring the spare images is may be omitted.

When the process for calculating A is terminated, the picture returns to a state of FIG. 21 on which 5.2, or the value of A acquired, is displayed on cell 2109. Then, length L in the y-direction of the examination area and a data sampling interval within length L are set.

Then, an image acquiring process is performed in a place where the length measurement is actually performed under the conditions of FIG. 21. Auto focus is performed on the length measurement area set in the examination recipe. Then, the area is irradiated with an electron beam and secondary electron image data is acquired from the area set in FIG. 21. The acquired image data comprises an averaged value of secondary electron signal intensities obtained in 16 scanning operations each performed from the upper left corner to the lower right corner of the visual field. The reason that the number of scanning operations was 16 is to reduce damage to the observation pattern. However, all the more, noise occurring in the observation image increased.

When the image of the area whose length was measured has been acquired, the analysis flow of FIG. 11 starts. The analysis mainly comprises step 1102 that obtains a dependability of roughness index $\sigma_m$ obtained from the observation image on the averaging parameter S, and step 1103 that fits the dependability and calculates contribution $\sigma_0$ of roughness present in the pattern, and a roughness index bias value $\sigma_e$ based on the influence of random noise. Since steps 1101 and 1102 were explained with reference to Embodiment 4, further description thereof will be omitted in this embodiment.

Figure 17:
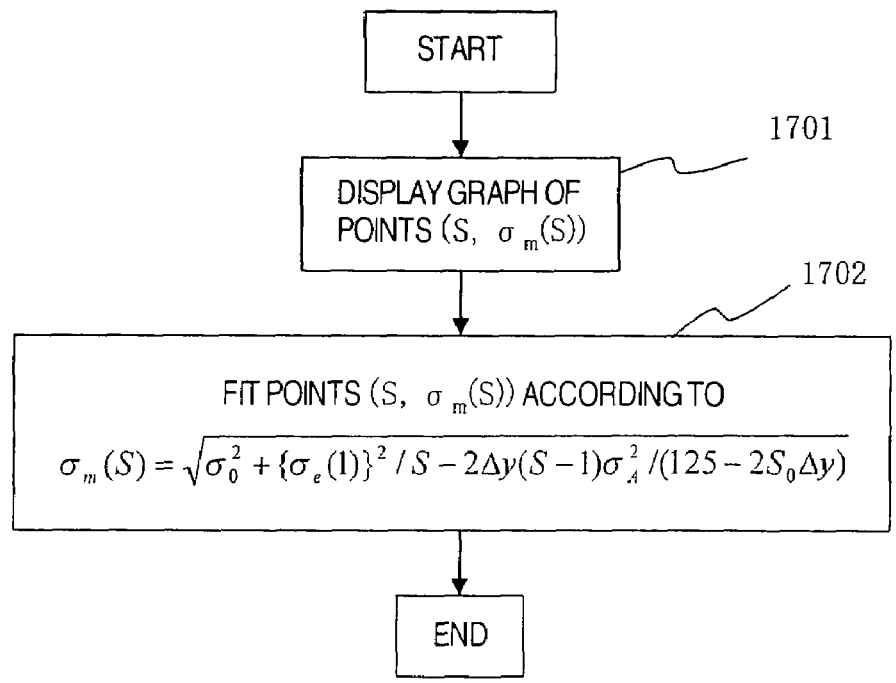
FIG. 17 is a flowchart indicative of the details of step 1102 in Embodiment 5 analyzing a roughness index obtained from the image data.

When up to step 1102 have been terminated, a data series $\{(S_i, \sigma_m (S_i))\}$: $\{(S_{min}, \sigma_m (S_{min}))\}$, $\{(S_{min}+1), \sigma_m (S_{min}+1)\}$, ..., $\{(S_{max}, \sigma_m (S_{max}))\}$ to calculate $\sigma_0$ and $\sigma_e$ is obtained. In step 1103, fitting is actually performed using the data series $\{(S_i, \sigma_m (S_i))\}$. Step 1103 will be next described in detail using FIG. 17.

First in step 1701, the data series $\{(S_{min}, \sigma_m (S_{min}))\}$: $\{(S_{min}+1), \sigma_m (S_{min}+1)\}$, ..., $\{(S_{max}, \sigma_m (S_{max}))\}$ thus obtained is displayed as a graph on monitor 2007.

Then in step 1702, fitting is performed by information processing means 2006 according to Ex. 9 using the value of A, 5.2, registered in the examination recipe corresponding to the wafer now under examination. The fitting parameters are two: $\sigma_0$ and $\sigma_e$ (1). As an algorithm for fitting purposes, the least squares method is used, thereby calculating those parameter values best describing $\sigma_m$ (S) obtained from the observation image. In this case, $\sigma_e$ (1) was used as $\sigma_e$. In the present embodiment, $\sigma_0$=2.25 nm and $\sigma_e$=0.95 nm were obtained. The results were displayed on the monitor picture and stored along with their identification codes to be used for registration in the storage of information processing means 2006. As the identification codes, identifiers corresponding to the wafers and examination places, a date when the roughness analysis (or image acquisition) was performed, or the user's peculiar management codes may be used.

Thus, the process of FIG. 11 was terminated and $\sigma_0$ and $\sigma_e$ were obtained. The $\sigma_0$ was used as an index representing a merit of the shape of the observation pattern and the $\sigma_0$ was recorded as an index indicative of a degree of noise involving the examining device. Since these two parameters can be obtained accurately and rapidly, the efficiency of pattern shape management and the productivity improved. In addition, the performance of the examination device can be monitored over a long time and hence productivity improved.

While in the present embodiment method 5-2 was used as the algorithm that performed the roughness analysis, another algorithm may be selected. In this case, the methods 5-1 to 5-3 are preferably set on the examination recipe such that the processor user can select one of the methods 5-1 to 5-3. For example, use of Ex. 11 instead of Ex. 9 in the fitting in step 1103 will lead to calculation of $\sigma_0$ and $\sigma_e$ in method 5-1. Use of Ex. 12 before the process of obtaining A and Ex. 13 in the fitting of step 1103 will lead to calculation of $\sigma_0$ and $\sigma_e$ in method 5-3. Since the same data series $\{(S_i, \sigma_m (S_i))\}$ is used even when any of those methods is used, implementation of this function is achieved only by correcting the software.

While in the present embodiment the set of image data in the area picked up when the parameter A was determined was used as it is as the set of image data in the place where the roughness analysis was performed, it is possible to newly pick up an image whose roughness analysis is to be performed. In that case, it is possible to use a different algorithm for the roughness analysis depending on the image pickup magnification. For example, a dialog box that specifies a place where the length measurement is actually made may be provided on the GUI picture of FIG. 21 such that the size of the image pickup area or the scanning area can be set on the GUI picture of FIG. 21. In this case, the algorithm for setting parameter A and the algorithm for performing the roughness analysis are provided separately. For example, the algorithm of method 5-2 is preferable for analysis of a low magnification image while method 4 is preferable for analysis of a picked-up image of a relatively high magnification. Thus, the arrangement may be such that a low magnification image of a relatively wide range is analyzed in method 5-2, thereby determining parameter A, a higher magnification image for analysis is acquired, and then roughness analysis is performed on the acquired image using the algorithm of method 4, thereby improving the analysis accuracy compared to the analysis using the same algorithm.

While in the present embodiment the edge roughness was calculated, the line width roughness may be used as an index instead of the line-edge roughness as in Embodiments 3 and 4. While in the present embodiment the in-line measurement was described, this method is applicable to the off-line measurement, of course. In the off-line measurement, the image of the examination area acquired is stored along with an appropriate image managing identifier, for example, a wafer identifier and coordinate information on the image pickup area in the information storage means. In the roughness analysis, the image data set is called and analyzed as requested. While in the present embodiment the examination area is illustrated as specified using a CAD image, the examination area may be specified with a real image. For example, a low-magnification wide-range real image can be acquired and displayed on the recipe setting picture of FIG. 21 or 22 and then a rectangular figure may be displayed superimposed thereon for area setting purposes.

Since the roughness analysis method described in the present embodiment does not involve Fourier's spectrum, calculation is simple and not time consuming. In addition, since a contribution to roughness of the high frequency components that cannot be detected due to noise reduction has been corrected accurately, the roughness analysis method ensure high analysis accuracy.

Embodiment 6

It is possible to predict results measured at different sampling intervals, using the results of measurement obtained in Embodiment 5. The present embodiment shows an example of calculation of a value of $\sigma_0$ which will be obtained when measured at smaller sampling intervals subsequent to the measurement made in Embodiment 5.

A value of 2.25 nm indicative of $\sigma_0$ obtained in Embodiment 5 corresponds to real dispersion of edge point positions obtained when a 200-nm-long line-edge was edge detected with an interval of 7.5 nm. However, evaluation of the influence of the accuracy on the device performance demands a roughness value corresponding to a sampling interval of 2 nm. Thus, $\sigma_0$ corresponding to the sampling interval of 2 nm was calculated according to the following procedures.

First, the value of A obtained from $\sigma_A=1.25$ nm is calculated in accordance with Ex. 9. More specifically, the user calls a prediction program from information processor 2006 through monitor 2007 and information input means 2008. When the program is called, a request to input a retrieval key to thereby call a result of the roughness analysis is displayed on monitor 2007. The user inputs the retrieval key accordingly. One of various identification codes described with reference to Embodiment 5 may be used as the retrieval key. The roughness analysis program may be arranged such that the roughness analysis result may be called on the examination recipe. When the retrieval key is inputted, the values of $\sigma_e$ already calculated as $\sigma_0$ is loaded on the memory of information processor 2006. A request to input $f_0$, $S_0$ and $\Delta y$ is displayed on monitor 2007. The device user inputs $1/f_0=2000$ nm, $S_0=3$ and $\Delta y=0.75$ nm according to the request. Then, the value of A is calculated according to Ex. 9. Then, Ex. 4 is integrated from $f_1$ to $f_2$ where $f_1=1/2\Delta y$ and $f_2=1/(2\cdot 2)$, using the value of A obtained. As a result, an evaluated value of A was 0.009 nm². From the above, a dispersion value obtained when the edge of 2000 nm was sampled at intervals of 2 nm was $2.25^2+0.009^2$ and $\sigma_0$ was obtained as the square root of this value. Since the significant figures were 0.01 nm, $\sigma_0$ obtained when the edge was sampled at intervals of 2 nm was 2.25 nm, which was the same value as that obtained when sampled at intervals of 7.5 nm.

As described above, a combination of the fifth method and the results of high and low magnification observations enables a value of edge roughness obtained by sampling the long line-edge at very fine intervals to be free from the influence of noise.

The high-accuracy pattern shape evaluating method and apparatus according to the present invention quantifies the influence of random noise due to the observation device included in line-edge roughness obtained from a pattern image in the examination process of a semiconductor manufacture and subtracts this quantified influence from the measured value, thereby enabling a value of roughness present in the pattern to be obtained with high accuracy. Thus, high-accuracy examination is achieved and productivity improves.

Since the influence of random noise arising from the observation device on the image is quantified, the observation requirements can be determined using this value. In addition, by managing this value over a long time, long time stability of the apparatus performance can be evaluated. Thus, the accuracy of the examination and productivity improve.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A pattern shape evaluating apparatus comprising:
   a scanning electron microscope detecting a secondary electron or reflected electron by irradiation of an electron beam to a specimen formed with line pattern, and retrieving a two-dimensional distribution data of the secondary electron signal or the reflected electron signal; and
   a data processing apparatus for processing the two-dimensional distribution data;
   wherein the data processing apparatus retrieves a plurality of edge points data of the line pattern from the two-dimensional distribution data;
   generates data set of the edge points with different averaging parameter that defines a range of averaging to longitudinal direction of the line pattern, by calculating an averaging process to the data set within a range defined by the averaging parameter;
   calculating a standard deviation of the roughness of the data set corresponding to each averaging parameter; and
   calculating a noise-caused bias of the roughness included based on a relationship between the standard deviation and the averaging parameter.

2. The pattern shape evaluating apparatus according to claim 1, said data processing apparatus calculates a real value and the noise-caused bias by fitting the standard deviation with the real value and the bias as fitting parameters.

3. The pattern shape evaluating apparatus according to claim 1, further comprising:
a monitor for displaying the noise-caused bias.

4. The pattern shape evaluating apparatus according to claim 3, wherein said monitor displays a request for the averaging parameter;
said data processing apparatus carries out the averaging process within a range defined by the entered value of the averaging process.

5. The pattern shape evaluating apparatus according to claim 4, wherein said data processing apparatus compensate the data set that is dropped in the averaging process.

6. The pattern shape evaluating apparatus according to claim 5, further comprising:
a storage means for storing first two-dimensional distribution data for the compensation;
wherein said monitor displays an image of the first two-dimensional distribution data and a request for selecting an area in the image,
said data processing apparatus calculates parameters used for the compensation using the first two-dimensional distribution data.

7. The pattern shape evaluating apparatus according to claim 6, wherein the storage means stores the second two-dimensional distribution data obtained at a higher magnification than the first two-dimensional distribution data; and
the data processing apparatus carries out the compensating operation on the data set of standard deviations calculated from the second two-dimensional distribution data, using the parameters calculated based on the first two-dimensional distribution data.

8. The pattern shape evaluating apparatus according to claim 5, wherein the data processing apparatus stores a plurality of different algorithms for the compensation.

9. The pattern shape evaluating apparatus according to claim 6, wherein said monitor displays CAD data corresponding to the selected area as the first two-dimensional distribution data.

10. A critical dimension measurement SEM equipped with a function calculating a roughness, including:
a scanning electron microscope for obtaining a data set of edge points used for the calculation of the roughness;
a data processing apparatus that calculates a roughness;
wherein said data processing apparatus has function comprised of:
averaging the edge points within a range defined by a predetermined averaging parameter;
calculating a standard deviation of the roughness using the data set of the averaged edge points;
calculating a relationship between the standard deviation and the averaging parameter; and
calculating a noise-caused bias in the roughness based on the relationship between the standard deviation and the averaging parameter.

11. The critical dimension measurement SEM according to claim 10, said function of the data processing apparatus further comprising:
calculating a real value and the noise-caused bias by fitting the standard deviation with the real value and the bias as fitting parameters.

12. The critical dimension measurement SEM according to claim 10, further comprising:
a monitor for displaying the noise-caused bias.

13. The critical dimension measurement SEM according to claim 12, wherein said monitor displays a request for the averaging parameter;
said function of the data processing apparatus further comprising:
calculating the averaging process within a range defined by the entered value of the averaging parameter.

14. The critical dimension measurement SEM according to claim 13, said function of the data processing apparatus further comprising:
compensating the data set that is dropped in the averaging process.

15. The critical dimension measurement SEM according to claim 14, further comprising:
a storage means for storing the first two-dimension distribution data for the compensation;
wherein said monitor displays an image of the first two-dimensional distribution data and a request for selecting an area in the image,
said function of the data processing apparatus further comprising:
calculating parameter used for the compensation using the first two-dimensional distribution data.

16. The critical dimension measurement SEM according to claim 15, wherein the storage means stores the second two-dimensional distribution data obtained at a higher magnification than the first two-dimensional distribution data;
said function of the data processing apparatus further comprising:
compensating the data set of standard deviations calculated from the second two-dimensional distribution data with using the parameters calculated based on the first two-dimensional distribution data.

17. The critical dimension measurement SEM according to claim 14, wherein the data processing apparatus stores a plurality of different algorithms for the compensation.

18. The critical dimension measurement SEM according to claim 15, wherein said monitor displays CAD data corresponding to the selected area as the first two-dimensional distribution data.

* * * * *